United States Patent
Masuda et al.

(10) Patent No.: US 8,334,371 B2
(45) Date of Patent: Dec. 18, 2012

(54) LACTIC ACID BACTERIA-DERIVED DOUBLE-STRANDED RNA

(75) Inventors: Ikuko Masuda, Noda (JP); Daisuke Kaneko, Noda (JP); Tadaomi Kawashima, Noda (JP); Noriko Tsuji, Tsukuba (JP); Akemi Kosaka, Tsukuba (JP)

(73) Assignee: Kikkoman Corporation, Chiba (JP)

( * ) Notice: Subject to any disclaimer, the term of this patent is extended or adjusted under 35 U.S.C. 154(b) by 304 days.

(21) Appl. No.: 12/452,405

(22) PCT Filed: Jul. 3, 2008

(86) PCT No.: PCT/JP2008/062066
§ 371 (c)(1),
(2), (4) Date: Jan. 26, 2010

(87) PCT Pub. No.: WO2009/005124
PCT Pub. Date: Jan. 8, 2009

(65) Prior Publication Data
US 2011/0159552 A1   Jun. 30, 2011

(30) Foreign Application Priority Data

Jul. 4, 2007 (JP) ................................. 2007-175694
Nov. 19, 2007 (JP) ................................. 2007-299243

(51) Int. Cl.
*C07H 21/02* (2006.01)
*C07H 21/04* (2006.01)
*C12Q 1/68* (2006.01)
*C12P 19/34* (2006.01)

(52) U.S. Cl. ........ 536/24.5; 435/6.1; 435/91.1; 435/325; 435/375

(58) Field of Classification Search .............. 536/24.1, 536/24.5; 435/6, 91.1, 325, 375
See application file for complete search history.

(56) References Cited

FOREIGN PATENT DOCUMENTS

| EP | 1 555 028 B1 | 9/2009 |
|---|---|---|
| JP | 05-252900 A | 10/1993 |
| JP | 06-080575 A | 3/1994 |
| JP | 07-228536 A | 8/1995 |
| JP | 08-099887 A | 4/1996 |
| JP | 09-002959 A | 1/1997 |
| JP | 09-124496 A | 5/1997 |
| JP | 09-188627 A | 7/1997 |
| JP | 09-227392 A | 9/1997 |
| JP | 10-167972 A | 6/1998 |
| JP | 10-309178 A | 11/1998 |
| JP | 2000-095697 A | 4/2000 |
| JP | 2003-113114 A | 4/2003 |
| JP | 2004-018469 A | 1/2004 |

(Continued)

OTHER PUBLICATIONS

*Lactic Acid Bacteria Sci. and Tech.*, pp. 316-334 (1996) (with an English translation).

(Continued)

*Primary Examiner* — Terra Cotta Gibbs
(74) *Attorney, Agent, or Firm* — Holtz Holtz Goodman & Chick, P.C.

(57) ABSTRACT

An immunoregulator that is safe and efficiently incorporated into cells along with a production process thereof are provided. Double-stranded RNA derived from lactic acid bacteria, an immunoregulator having for an active ingredient thereof double-stranded RNA derived from lactic acid bacteria, and a process for producing double-stranded RNA derived from lactic acid bacteria are provided. Bacteria cells of a strains of lactic acid bacteria such as genus *Tetragenococcus*, genus *Pediococcus*, genus *Lactobacillus*, genus *Streptococcus* or genus *Leuconostoc* are able to produce double-stranded RNA having immunoregulatory action therein.

6 Claims, 19 Drawing Sheets

FOREIGN PATENT DOCUMENTS

| | | |
|---|---|---|
| JP | 2006-028047 A | 2/2006 |
| JP | 2006-232790 A | 9/2006 |
| JP | 2006-325540 A | 12/2006 |
| WO | WO 2005/115420 A1 | 12/2005 |

OTHER PUBLICATIONS

C. Lawrence et al, "Production of Interleukin-12 by Murine Macrophages in Response to Bacterial Peptidoglycan", *Infection and Immunity*, vol. 66, No. 10, pp. 4947-4949 (Oct. 1998).

M.G. Cleveland et al, "Lipoteichoic Acid Preparations of Gram-Positive Bacteria Induce Interleukin-12 . . .", *Infection and Immunity*, vol. 64, No. 6, pp. 1906-1912 (Jun. 1996).

H.D. Brightbill et al, "Host Defense Meachanisms Triggered by Microbial Lipoproteins Through Toll-Like Receptors", *Science*, vol. 285, pp. 732-736 (Jul. 1999).

A.M. Krieg et al, "CpG motifs in bacterial DNA trigger direct B-cell activation", *Nature*, vol. 374, pp. 546-549 (Apr. 1995).

M.J. Skeen, "Regulation of Murine Macrophase IL-12 Production", *Journal of Immunology*, vol. 156, pp. 1196-1206 (1996).

E. Masse et al, A small RNA regulates the expression of genes involved in iron metabolism in *Escherichia coli*, *Proc. Nat'l Academy of Sci.*, vol. 99, No. 7, pp. 4620-4625 (Apr. 2002).

*Nikkei Biotech.*, 552, pp. 5-6 (2004) (with an English translation).

I. Nishimura, "*Tetragenococcus halophilus* KK221 Kabu (Th221 Kabu) no Nihonsa RNA wa TLR3 . . .", *J. of Japan Society for Lactic Acid Bacteria*, vol. 19, No. 2, p. 117 (Jun. 2008) (with an English translation).

H. Kitazawa et al, "Interferon Induction in Murine Peritoneal Macrophage by Stimulation with *Lasctobacillus acidophilus*", *Microbiology and Immunology*, vol. 36, No. 3, pp. 311-315 (1992).

K. Matsumura et al, "Interferon Induction by Murine Peritoneal Macrophage Stimulated with *Lactobacillus gasseri*", *Animal Science and Technology*, vol. 63, No. 11, pp. 1157-1159 (1992).

B. Solis-Pereyra et al, "Role of food in the stimulation of cytokine production", *The American Journal of Clinical Nutrition*, vol. 66, No. 4, pp. 299-303 (1991).

B.S. Pereyra et al, "Interferon induction by *Lactobacillus bulgaricus* and *Streptococcus thermophilus* in mice", *European Cytokine Network*, vol. 2, No. 4, pp. 299-303 (1991).

S. Kabayama et al, "Enhancing effects of food components on the production of interferon β from animal cells suppressed by stress hormones", *Cytotechnology*, vol. 23, No. 1-3, pp. 119-125 (1997).

Y. Fukui et al, "Analysis of immunostimulating effect of *Lactobacillus brevis* KB290 in mice: a nutrigenomics approach", *Shokohin to kaihatsu*, vol. 42, No. 5, pp. 85-87 (2007) (with English translation).

U.S. Appl. No. 12/452,414 deposited Dec. 29, 2009, Confirmation No. 6207.

Debra A. Peattie et al., "A 'Bulged' Double Helix in a RNA-Protein Contact Site," *Proc. Natl. Acad. Sci. USA*, 1981, vol. 78, No. 12, pp. 7331-7335.

Notification of Reasons for Rejections dated Aug. 30, 2011 in Japanese patent application 2009-521668.

H. Kitazawa et al, "At Oligonucleotides Including B lymphocyte Activation Exist in Probiotic *Lactobacillus gassen*", *Int. J. Food Microbiol.*, vol. 65, No. 3, pp. 149-162 (2001).

H. Kitazawa et al, "Immunostimulatory Oligonucleotide, CpG-like Motif Exists in *Lactobacillus delbrueckii ssp. bulgaricus* NIAI B6", *Int. J. Food Microbiol.*, vol. 85, No. 1-2, pp. 11-21 (2003).

N. Takahashi et al, An Immunostimulatory DNA Sequence from a Probiotic Strain of *Bifidobacterium longum* Inhibits IgE Production in vitro, *FEMS Immuno. Med. Microbiol.*, vol. 46, No. 3, pp. 461-469 (2006).

I. Nishimura, "*Tetragenococcus halophilus* KK221 Kabu (Th221 Kabu) no Nihonsa RNA wa TAL3 o Kaishite Kogen Teiji . . .", *Journal of Japan Soc. for Lactic Acid Bacteria*, vol. 19, No. 2, p. 117 (2008).

S. Masuda et al, "Immunomodulatory Effect of Halophilic Lactic Acid Bacterium *Tetragenococcus halophilus* Th221 from Soy Sauce Moromi . . .", *Int. J. Food Microbiol.*, vol. 121, No. 3, pp. 245-252 (2008).

S. Ishikawa et al, "MyD88 but Not TLR2, 4 or 9 is Essential for IL-12 Induction by Lactic Acid Bacteria", *Biosci. Biotechnol. Biochem*, vol. 71, No. 12, pp. 3026-3032 (2007).

Kuwahara et al., "Delivery of dsRNA with lactic acid bacteria for RNA interference," *Nucleic Acids Symposium Series*, No. 51, (2007) pp. 413 to 414.

Supplementary European Search Report dated Jun. 4, 2010 in EP 08 77 7818.

Chen et al. (Isolation and characterization of lactic acid bacteria from suan-tsai (fermented mustard), a traditional fermented food in Taiwan, 2006, Journal of Applied Microbiology, vol. 101, pp. 125-130).

LACTIC ACID BACTERIA-DERIVED DOUBLE-STRANDED RNA

This application is the United States national phase application of International Application PCT/JP2008/062066 filed Jul. 3, 2008.

TECHNICAL FIELD

The present invention relates to lactic acid bacteria-derived double-stranded RNA and a production process thereof.

BACKGROUND ART

The body's immune system plays an important role in defending against infections caused by microorganisms such as bacteria, yeast, molds and viruses, against tumors and in the onset of allergies. However, the immune system is known to decrease in function due to aging, stress and illnesses such as cancer. Thus, there is a need for a safe and inexpensive immunoregulator that is highly effective for preventing microbial infections, demonstrating antitumor activity and preventing allergies.

Lactic acid bacteria are known to be safe microorganisms that are commonly consumed in the diet. In addition, they have also been reported to have various functionalities, such as intestinal regulatory action, serum cholesterol lowering action, immunoactivating action and immunoregulatory action such as antiallergic action (see, for example, Non-Patent Document 1). Examples of lactic acid bacteria commercially available in the form of probiotic lactic acid bacteria having immunoregulatory action include lactic acid bacteria belonging to the genera *Streptococcus* and *Lactobacillus*. These lactic acid bacteria are used to ferment dairy products (such as yogurt and yogurt drinks).

Immunoactivators and immunoregulators such as antiallergics having lactic acid bacteria as an active ingredient thereof are known in the prior art (see, for example, Patent Documents 1 to 12). Components reported to be involved with these immunoregulators having lactic acid bacteria as an active ingredient thereof include cell wall components in the form of peptidoglycans (see, for example, Non-Patent Document 2), lipoteichoic acid (see, for example, Non-Patent Document 3), lipoproteins (see, for example, Non-Patent Document 4), nucleic acids (see, for example, Non-Patent Documents 5 and 6) and heat shock proteins (see, for example, Non-Patent Document 7).

Among these related components, those reported to be nucleic acid components include the CpG motif (see, for example, Non-Patent Document 5) and the AT motif (see, for example, Non-Patent Document 6) of DNA.

At present, ten types of Toll-like receptors (TLR) are known to exist in humans. TLR are a type of protein present in the cell membrane that recognize extracellular pathogens and the like, and produce interferon and cytokines by transmitting that information inside cells.

In particular, TLR3 is known to recognize viral double-stranded RNA and induce interferon β promoter activation and interferon β production independent of MyD88. Interferon β activates dendritic cells and causes them to produce inflammatory cytokines such as interleukin 12 and TNF. Moreover, interleukin 12 establishes cellular immunity by inducing differentiation of naive T cells into type I helper T cells (Th1).

Double-stranded RNA refers to a structure uniquely observed in RNA viruses. Double-stranded RNA is formed when a virus infects host cells and replicates its virus genome by using host systems. In addition, double-stranded RNA is also present in the genome of double-stranded RNA viruses.

In addition, although reports on the subject are extremely rare, bacteria are also known to form double-stranded RNA under certain stressful conditions. In *Escherichia coli*, for example, a low molecular weight RNA known as RyhB is synthesized when the organism is subjected to iron ion depletion. This low molecular weight RNA is known to form partial base pairs with mRNA encoding iron-binding protein containing sodB mRNA, resulting in the formation of double-stranded RNA (see, for example, Non-Patent Document 8). However, whether or not this double-stranded RNA has an immunoregulatory action is unknown. In addition, there have thus far been no reports indicating the presence of double-stranded RNA in lactic acid bacteria.

As has been described above, although viral double-stranded RNA is considered to be preferable as an immunoactivator since it induces cellular immunity mediated by TLR3, use of the virus itself as an immunoactivator is not realistic in terms of safety, and modifications are required to ensure safety.

One solution involves the use of artificial double-stranded RNA for which safety has been ensured. In actuality, an artificial double-stranded RNA in the form of PolyI:PolyC has long been studied for use as an anticancer agent or antiviral agent due to its interferon-inducing effect. However, a system for enabling the required drug to be effectively incorporated into cells is required for general use in the body. For example, in order to allow PolyI:PolyC to act effectively in the body, it is necessary to incorporate it in the form of a liposome preparation (see, for example, Non-Patent Document 9).

In view of these circumstances, there is a need for a double-stranded RNA that can be used as an immuno activator, which is safe, and which is effectively incorporated into cells.

Patent Document 1: Japanese Unexamined Patent Application, First Publication No. H6-80575
Patent Document 2: Japanese Unexamined Patent Application, First Publication No. H9-227392
Patent Document 3: Japanese Unexamined Patent Application, First Publication No. H7-228536
Patent Document 4: Japanese Unexamined Patent Application, First Publication No. H10-167972
Patent Document 5: Japanese Unexamined Patent Application, First Publication No. H8-99887
Patent Document 6: Japanese Unexamined Patent Application, First Publication No. H5-252900
Patent Document 7: Japanese Unexamined Patent Application, First Publication No. 2003-113114
Patent Document 8: Japanese Unexamined Patent Application, First Publication No. 2004-26729
Patent Document 9: Japanese Unexamined Patent Application, First Publication No. 2004-18469
Patent Document 10: Japanese Unexamined Patent Application, First Publication No. 2000-95697
Patent Document 11: Japanese Unexamined Patent Application, First Publication No. H10-309178
Patent Document 12: Japanese Unexamined Patent Application, First Publication No. H9-2959
Non-Patent Document 1: Lactic Acid Bacteria Science and Technology, Japan Scientific Societies Press (1996)
Non-Patent Document 2: Lawrence C. and Nauciel C.: Infection and Immunity, 1998, 66, 4947-4949
Non-Patent Document 3: Cleceland M. G., et al.: Infection and Immunity, 1996, 64, 1906-1912
Non-Patent Document 4: Brightbill H. D., et al.: Science, 1999, 30, 732-736

Non-Patent Document 5: Krieg A. M., et al.: Nature, 1995, 374, 546-549

Non-Patent Document 6: Kitazawa H., et al.: Int. J. Food Microbiol., 2001, 65, 149-162

Non-Patent Document 7: Skeen M. J., et al.: Journal of Immunology, 1996, 156, 1196-1206

Non-Patent Document 8: Masse E. and Gottesman S., Proc. Natl. Acad. Sci. USA, 2002, 99, 4620-4625

Non-Patent Document 9: Nikkei Biotech, 552, 5 "Nippon Shinyaku Co. Ltd. Increased Dosage of the Double-Stranded Nucleic Acid Drug PolyI:PolyC Currently Being Tested in US"

DISCLOSURE OF THE INVENTION

Problems to be Solved by the Invention

An object of the present invention is to provide an immunoregulator that has immunoregulatory action, is safe and which is efficiently incorporated into cells.

Means for Solving the Problems

As a result of conducting extensive studies relating to lactic acid bacteria having immunoregulatory action and their cellular components in order to solve the aforementioned problems, the inventors of the present invention found that double-stranded RNA derived from lactic acid bacteria has immunoregulatory action.

In addition, the cells of lactic acid bacteria belong to genus *Tetragenococcus*, genus *Pediococcus*, genus *Lactobacillus*, genus *Streptococcus* and genus *Leuconostoc* were determined to produce double-stranded RNA having immunoregulatory action within their cells. It was also found that the content of double-stranded RNA having immunoregulatory action in genus *Tetragenococcus*, which is a typical genus of lactic acid bacteria used in the brewing of soy sauce, can be considerably increased by culturing in the presence of stress.

Namely, according to the present invention, a safe and inexpensive immunoactivator or immunoregulator such as an antiallergic can be provided.

Namely, the present invention relates to the following:
(1) double-stranded RNA derived from lactic acid bacteria;
(2) the double-stranded RNA derived from lactic acid bacteria described in (1) above, wherein the lactic acid bacteria are one strain or two or more strains selected from genus *Tetragenococcus*, genus *Pediococcus*, genus *Lactobacillus*, genus *Streptococcus* and genus *Leuconostoc*;
(3) the double-stranded RNA derived from lactic acid bacteria described in (1) and (2) above, wherein the immunoregulatory action activates a TRIF-dependent signal transduction pathway or MyD88-dependent signal transduction pathway;
(4) the double-stranded RNA derived from lactic acid bacteria described in (3) above, wherein activation of the TRIF-dependent signal transduction pathway or the MyD88-dependent signal transduction pathway is activation of Toll-like receptor 3 (TLR3);
(5) an immunoregulator having for an active ingredient thereof double-stranded RNA derived from lactic acid bacteria;
(6) the immunoregulator described in (5) above, wherein the lactic acid bacteria are one strain or two or more strains selected from genus *Tetragenococcus*, genus *Pediococcus*, genus *Lactobacillus*, genus *Streptococcus* and genus *Leuconostoc*;
(7) a process for producing double-stranded RNA derived from lactic acid bacteria, comprising: producing double-stranded RNA within bacteria cells by culturing lactic acid bacteria under stressful conditions;
(8) the process for producing double-stranded RNA derived from lactic acid bacteria described in (7) above, wherein the lactic acid bacteria are one strain or two or more strains selected from genus *Tetragenococcus*, genus *Pediococcus*, genus *Lactobacillus*, genus *Streptococcus* and genus *Leuconostoc*; and,
(9) a process for producing double-stranded RNA derived from lactic acid bacteria, characterized by: producing double-stranded RNA within bacteria cells by culturing lactic acid bacteria belonging to the genus *Tetragenococcus* in lactic acid bacteria culture medium having a salt content of 0.5 to 25%.

Figure 10:
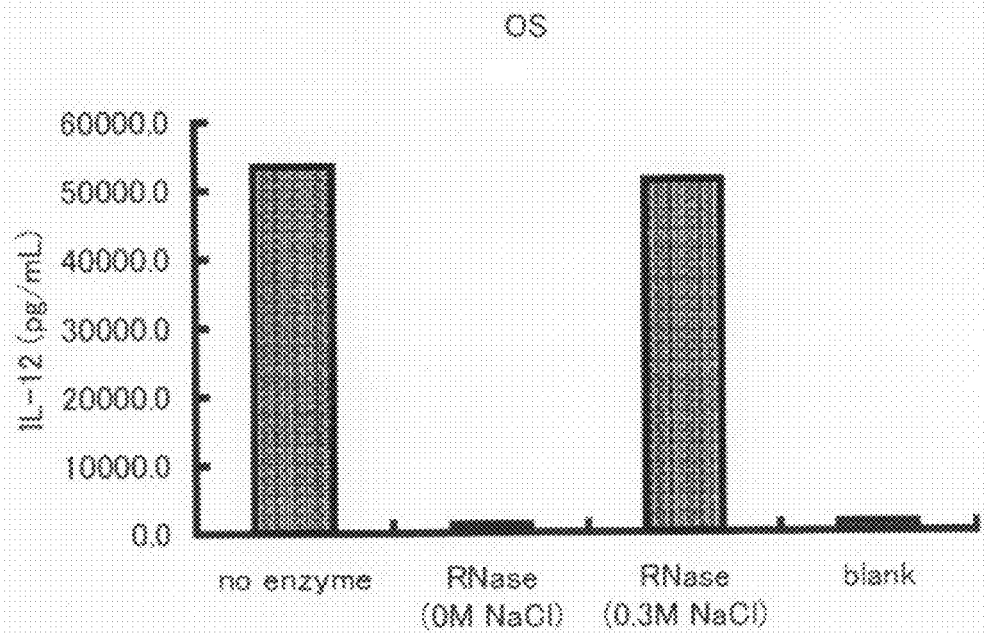
Figure 11:
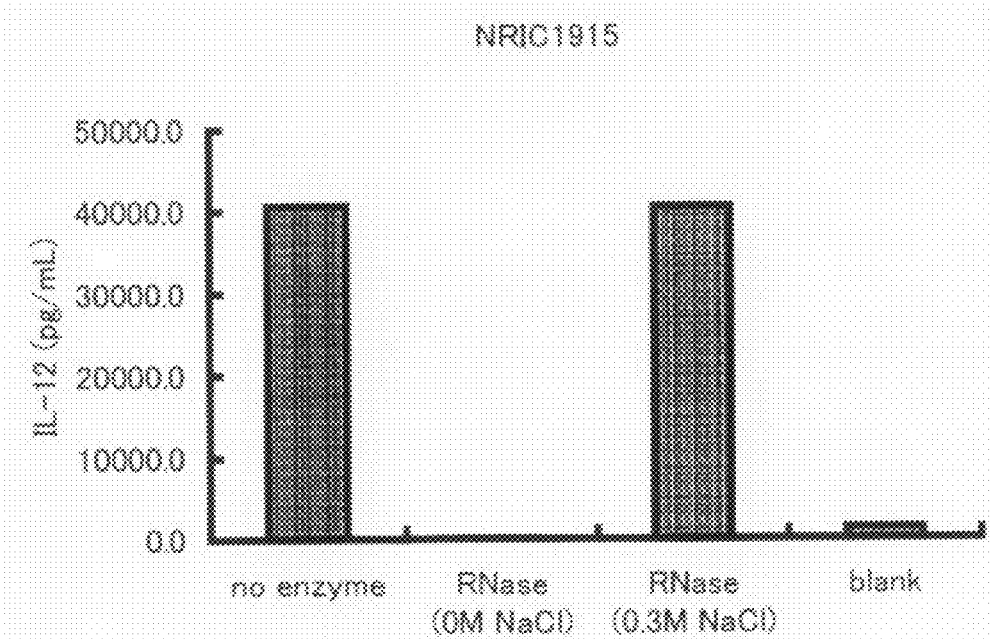
Figure 12:
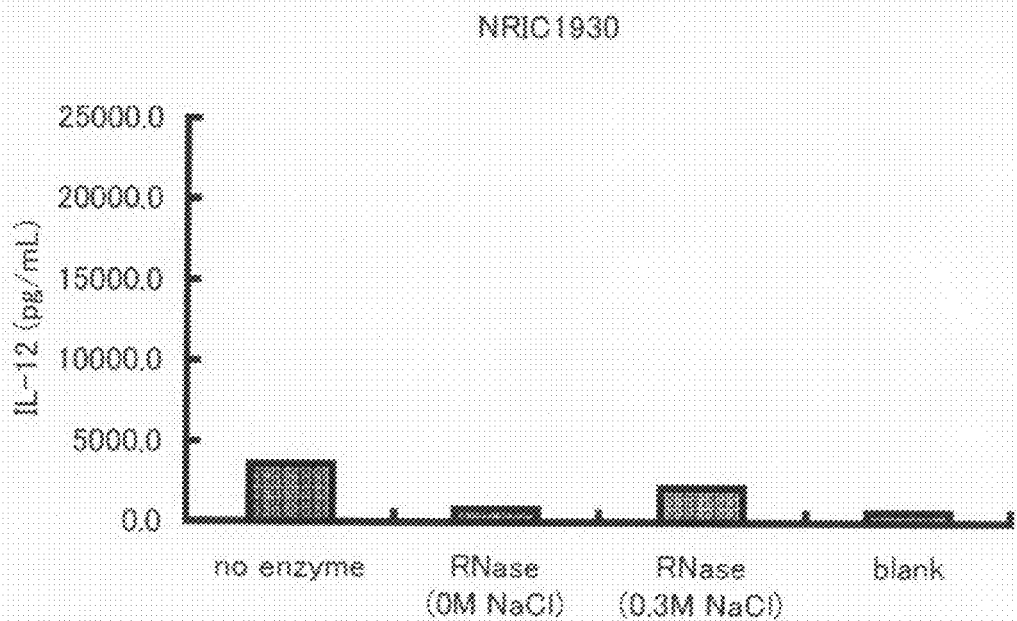
Figure 13:
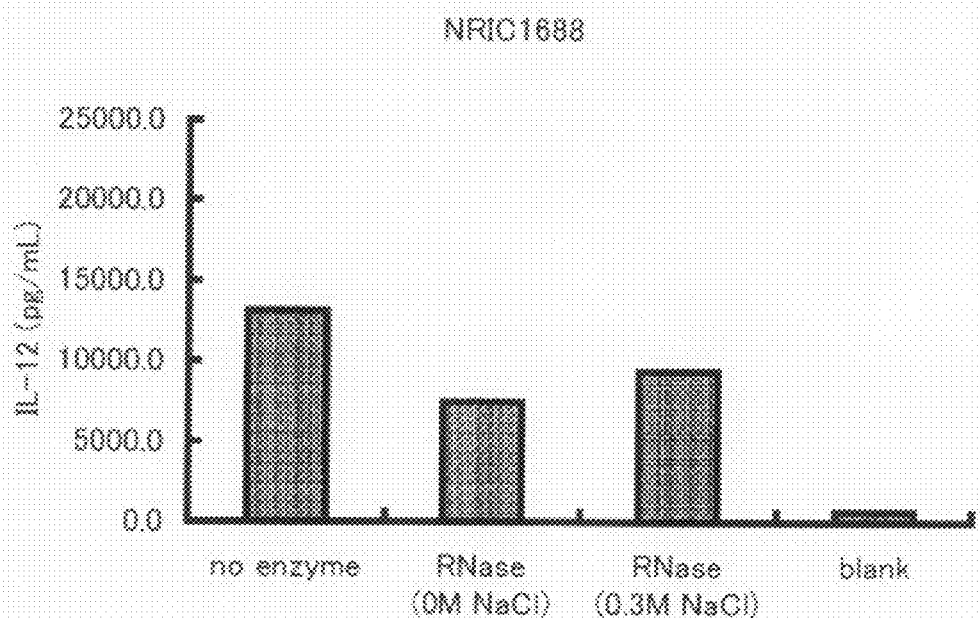
Figure 14:
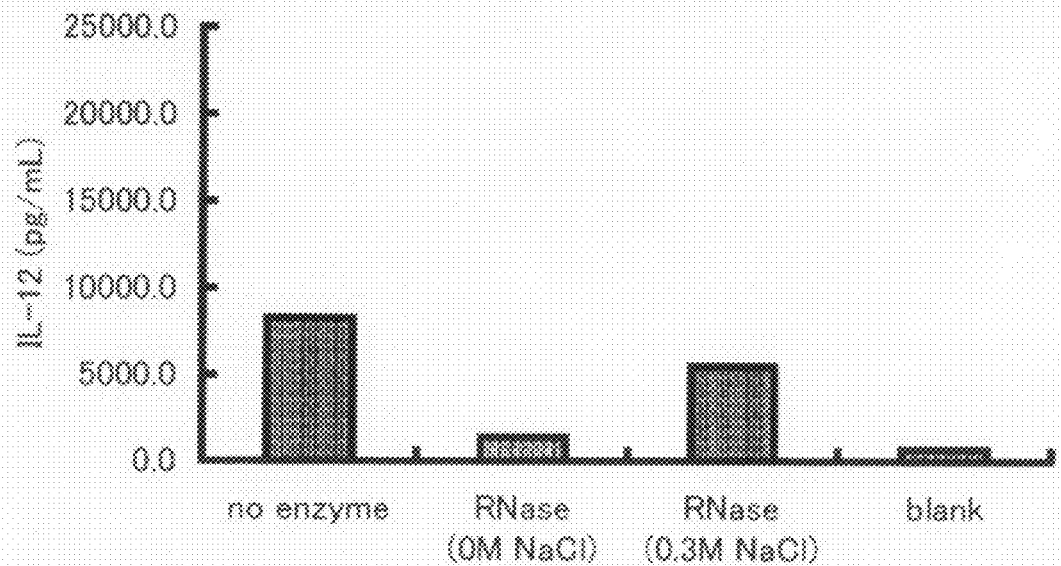
Figure 15:
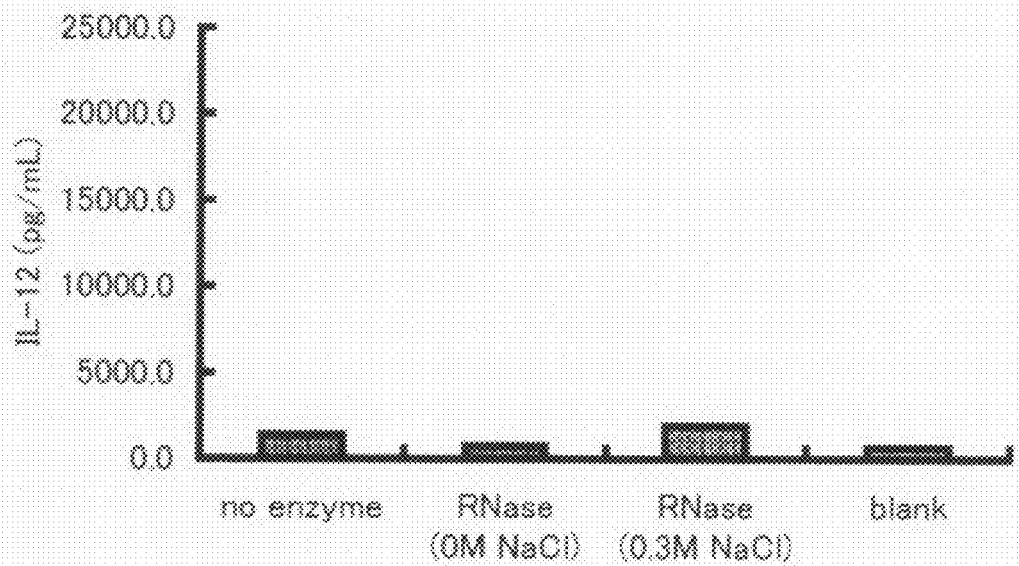
Figure 16:
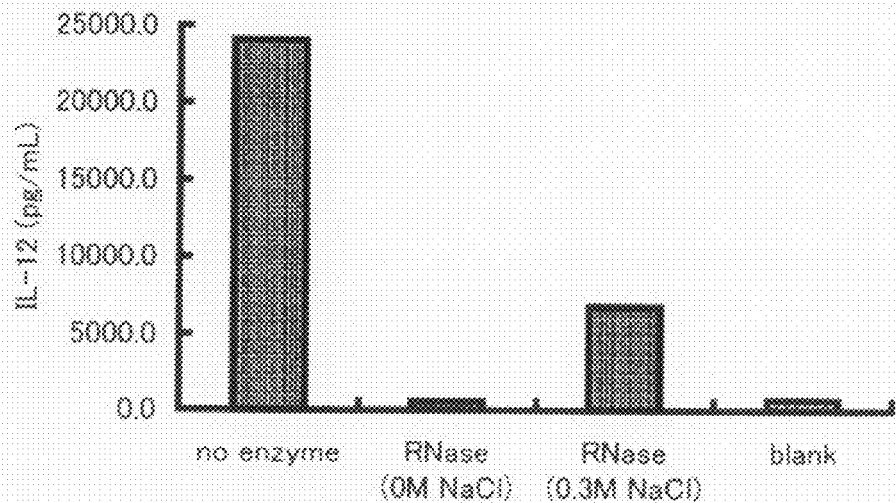
Figure 17:
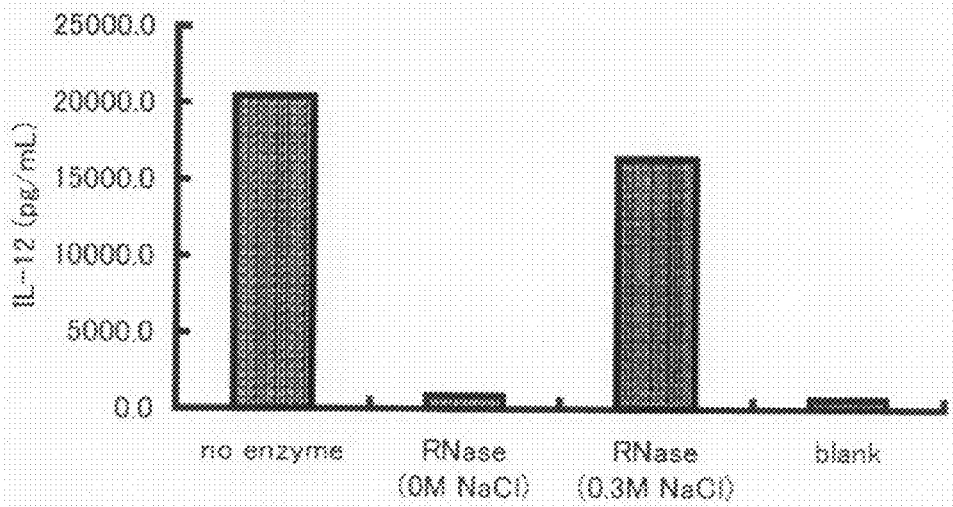
Figure 18:
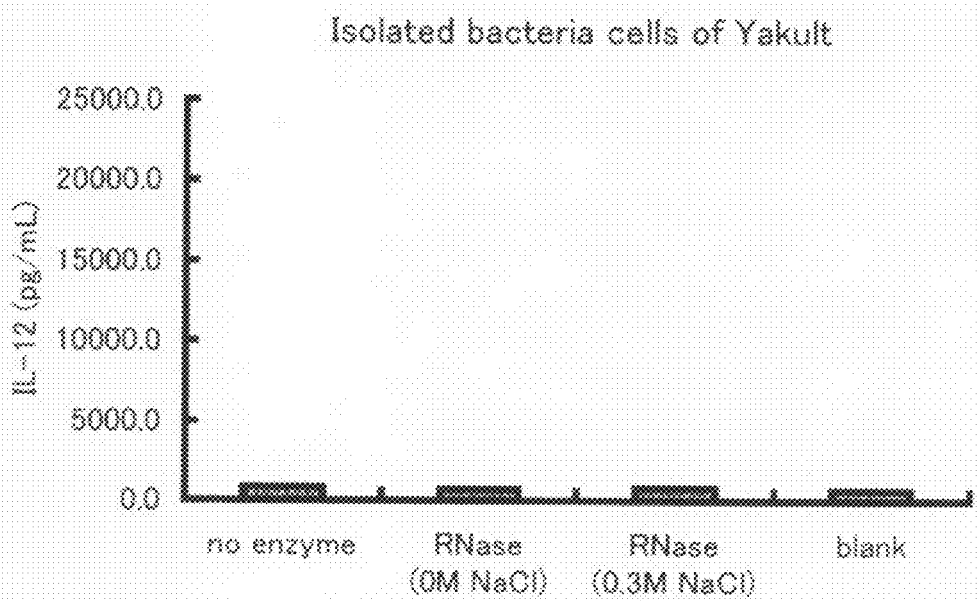
Figure 19:
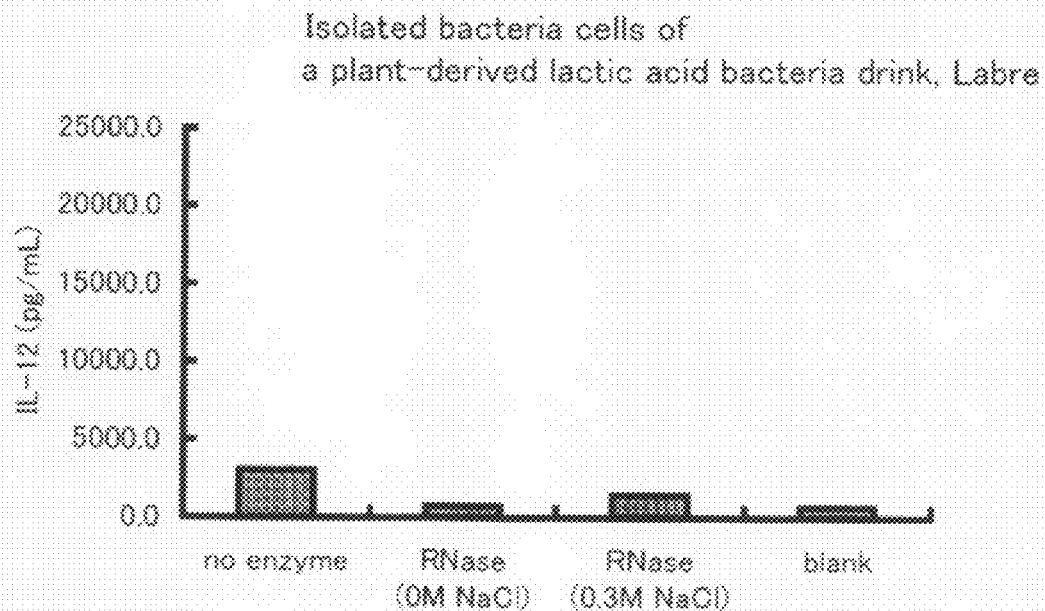
Figure 20:
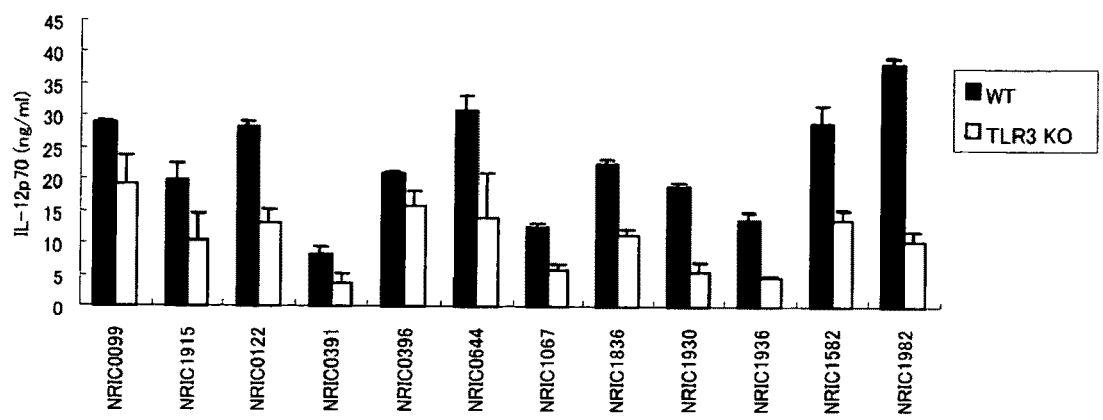
Figure 21:
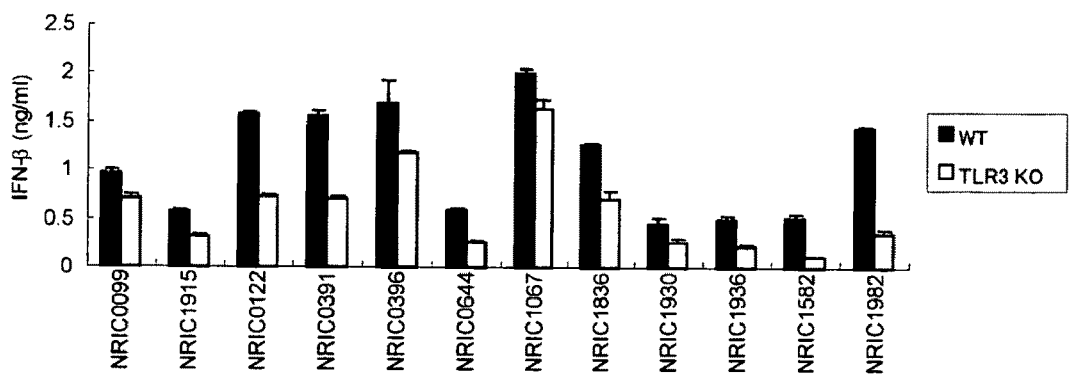
Figure 22:
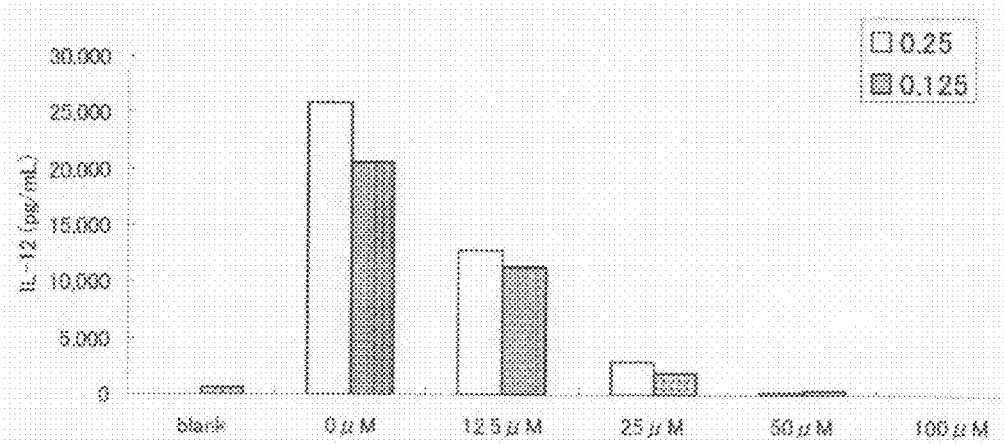
Figure 23:
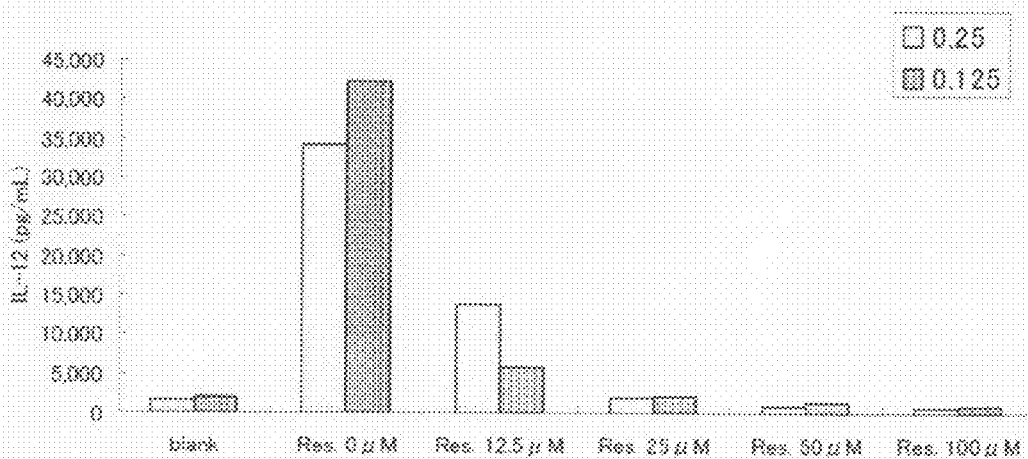
Figure 24:
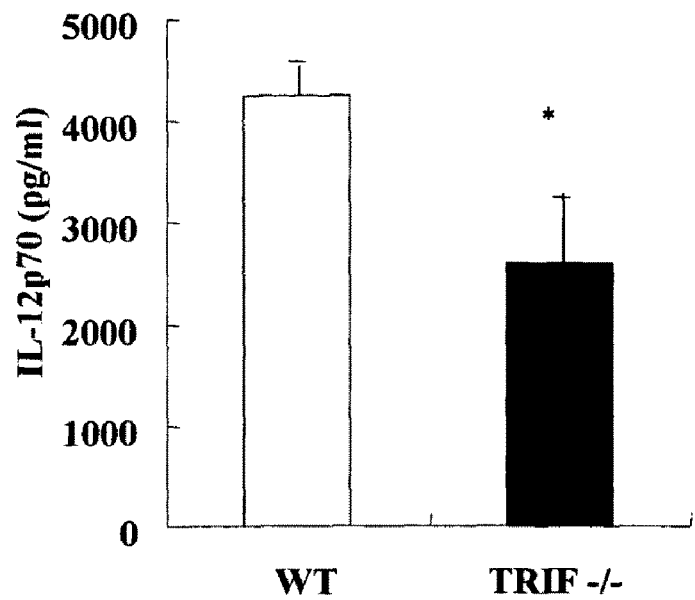
Figure 25:
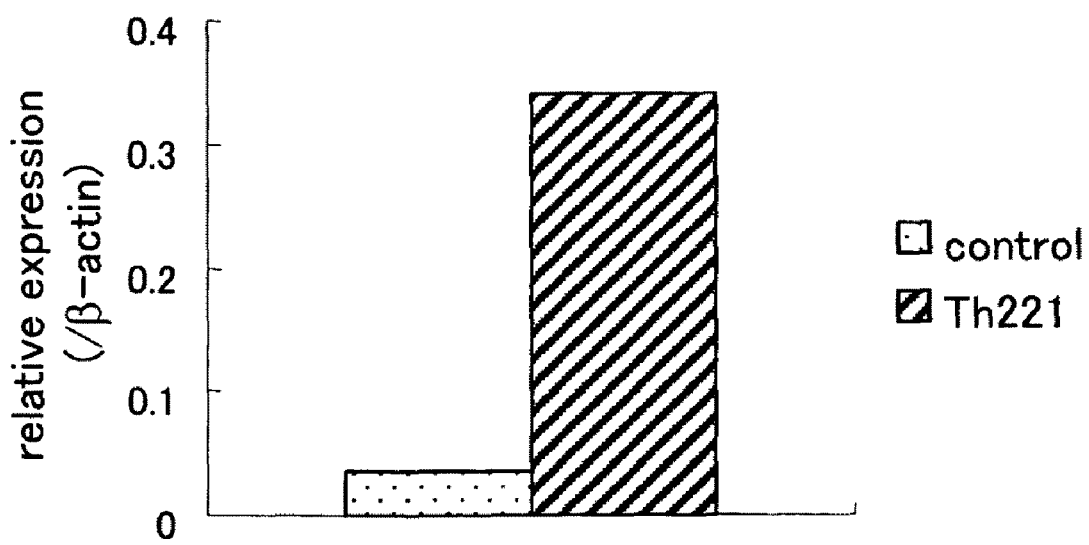
Figure 26:
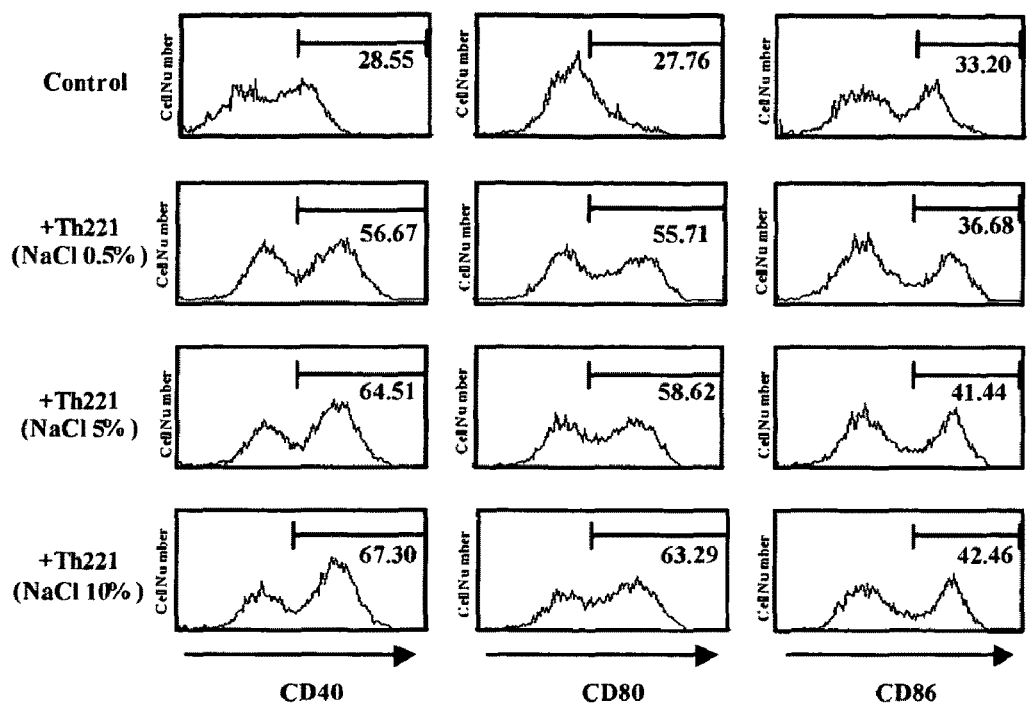
Figure 27:
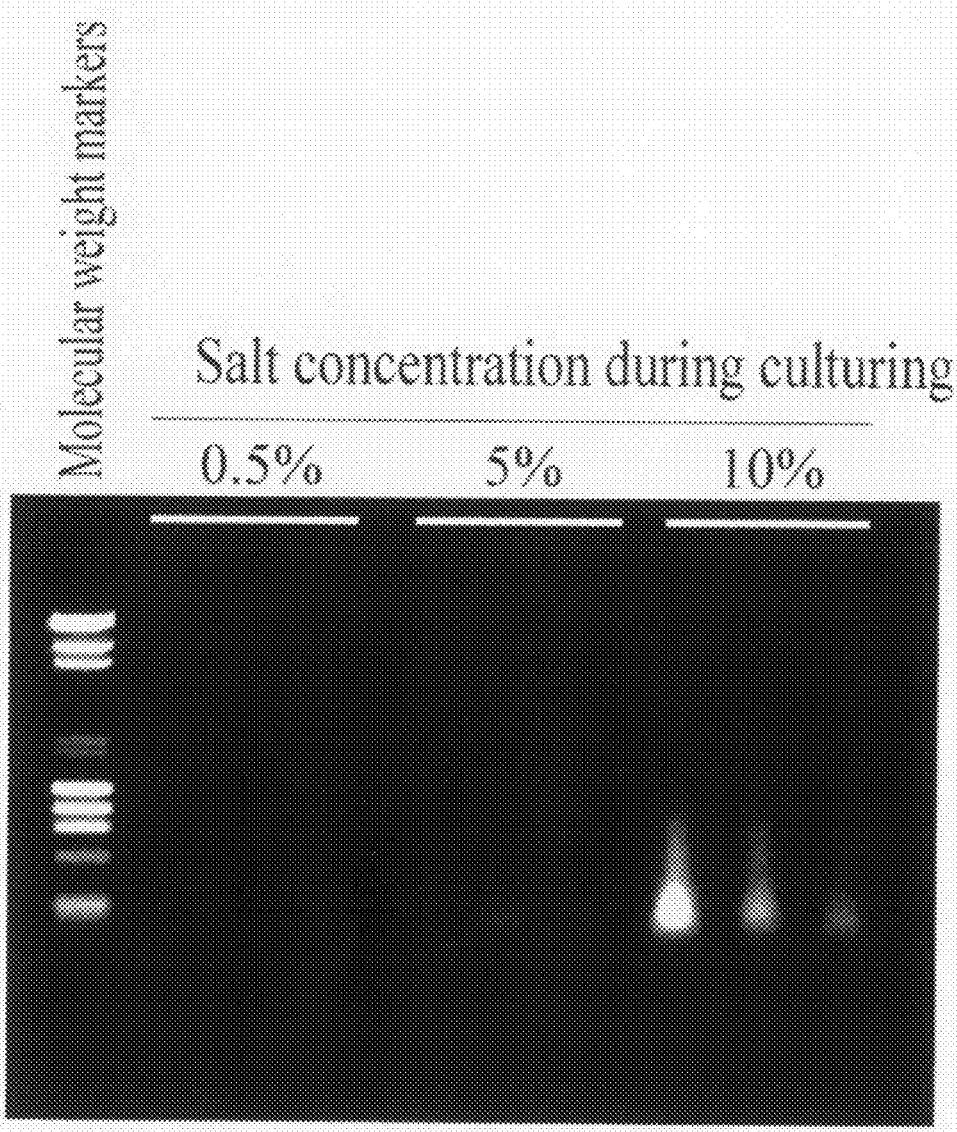
Figure 28:
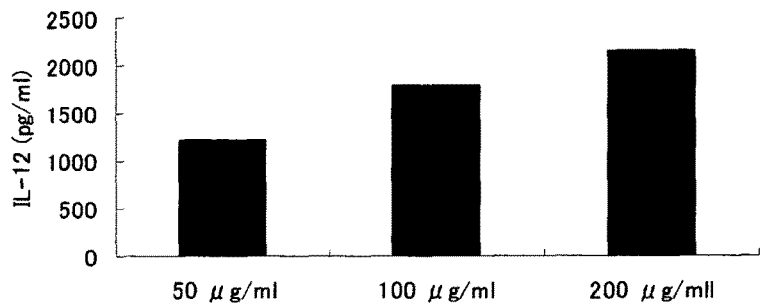
Figure 29:
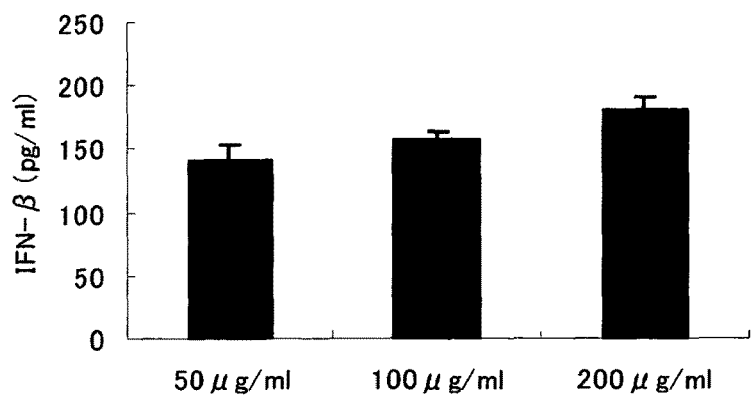
Figure 30:
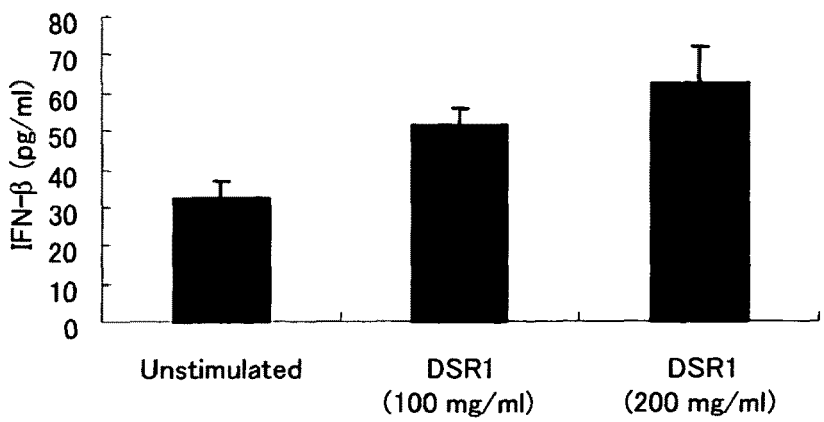
Figure 31:
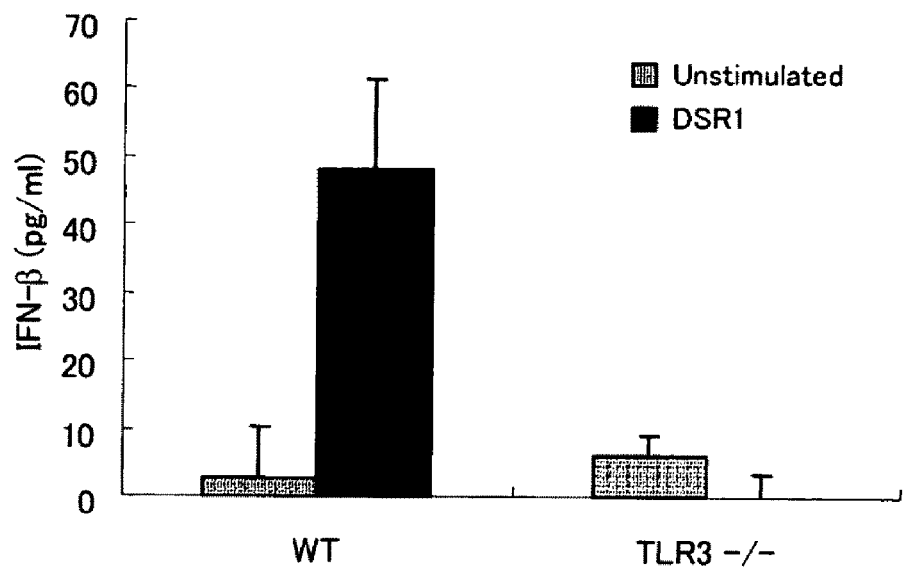
Figure 32:
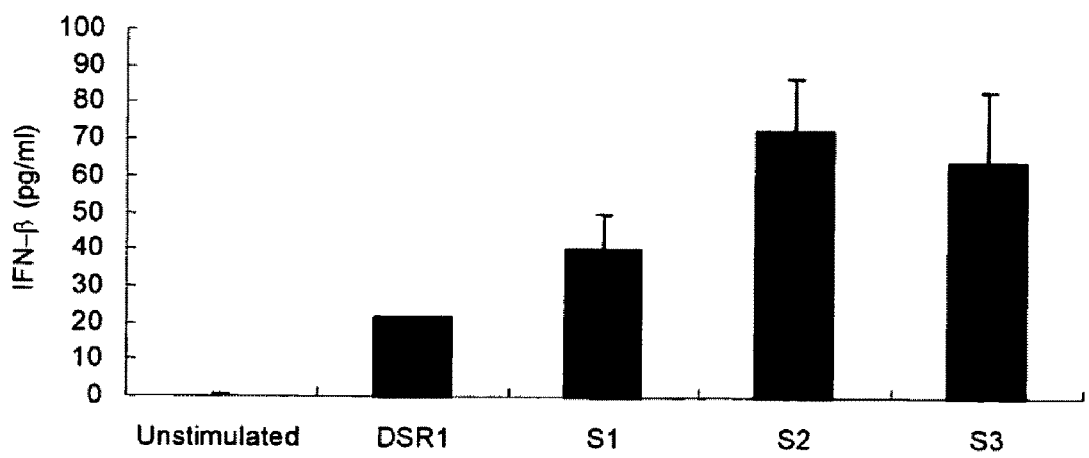
Figure 33:
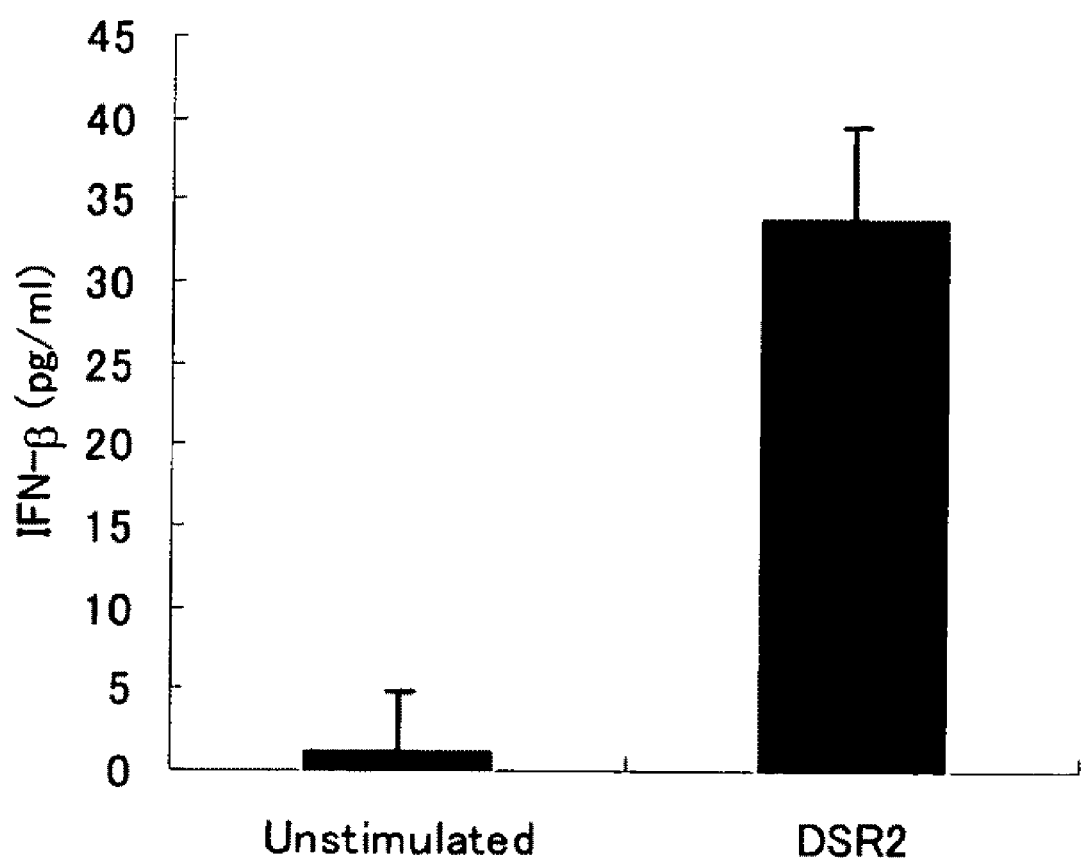
Figure 34:
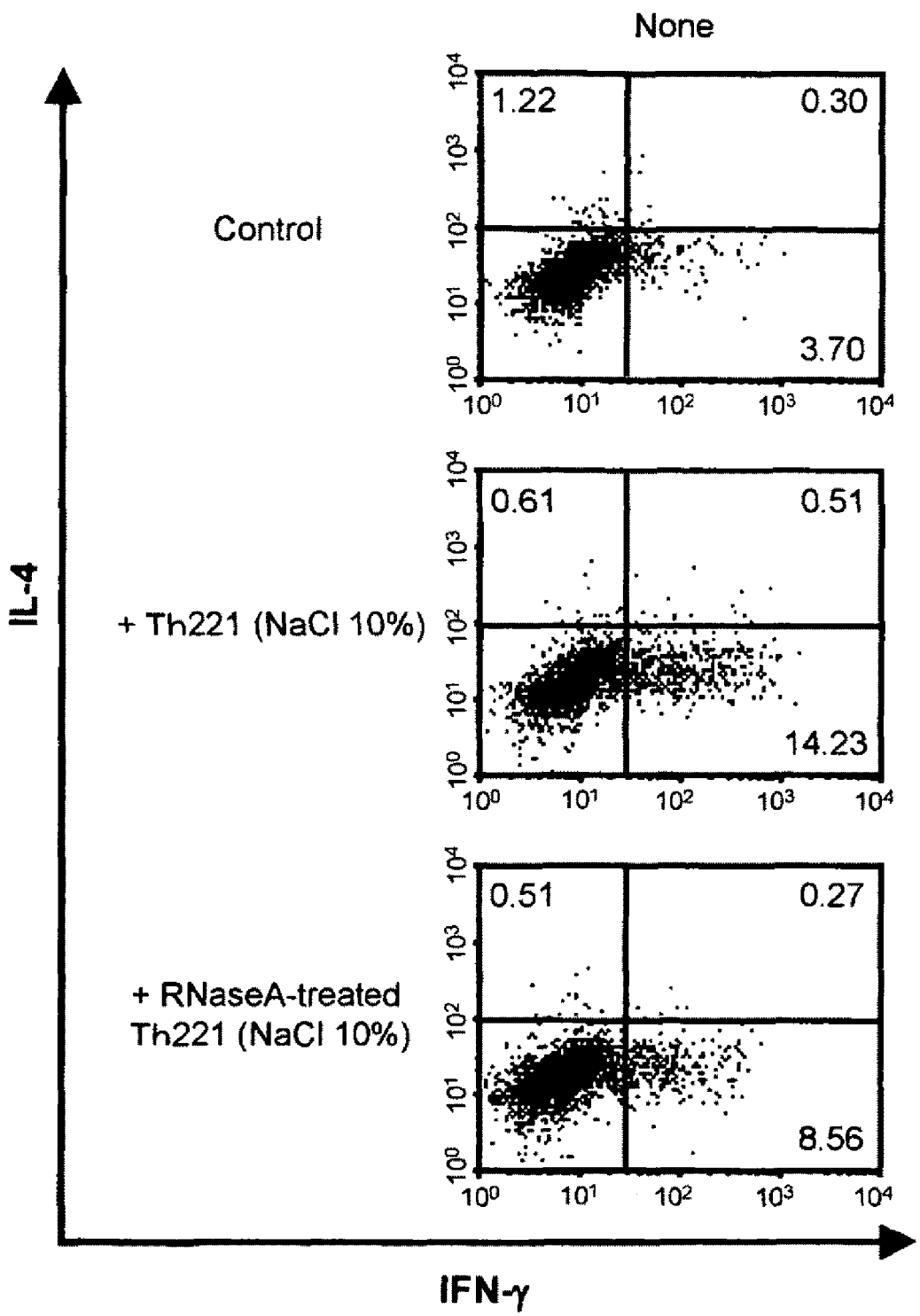

FIG. 10 is a graph showing the results of a test of promotion of interleukin 12 production in peritoneal exudate macrophage cells by *Pediococcus pentosaceus* strain OS cells and cells treated with bovine pancreas-derived RNase A (in the absence of NaCl and in the presence of 0.3 M NaCl);

FIG. 11 is a graph showing the results of a test of promotion of interleukin 12 production in peritoneal exudate macrophage cells by *Pediococcus pentosaceus* strain NRIC 1915 cells and cells treated with bovine pancreas-derived RNase A (in the absence of NaCl and in the presence of 0.3 M NaCl);

FIG. 12 is a graph showing the results of a test of promotion of interleukin 12 production in peritoneal exudate macrophage cells by *Lactobacillus plantarum* strain NRIC 1930 cells and cells treated with bovine pancreas-derived RNase A (in the absence of NaCl and in the presence of 0.3 M NaCl);

FIG. 13 is a graph showing the results of a test of promotion of interleukin 12 production in peritoneal exudate macrophage cells by *Lactobacillus delbrueckii* subspecies *bulgaricus* strain NRIC 1688 cells and cells treated with bovine pancreas-derived RNase A (in the absence of NaCl and in the presence of 0.3 M NaCl);

FIG. 14 is a graph showing the results of a test of promotion of interleukin 12 production in peritoneal exudate macrophage cells by *Lactobacillus delbrueckii* subspecies *lactis* strain NRIC 1683 cells and cells treated with bovine pancreas-derived RNase A (in the absence of NaCl and in the presence of 0.3 M NaCl);

FIG. 15 is a graph showing the results of a test of promotion of interleukin 12 production in peritoneal exudate macrophage cells by *Lactobacillus brevis* strain NRIC 1713 cells and cells treated with bovine pancreas-derived RNase A (in the absence of NaCl and in the presence of 0.3 M NaCl);

FIG. 16 is a graph showing the results of a test of promotion of interleukin 12 production in peritoneal exudate macrophage cells by *Streptococcus thermophilus* strain NRIC 0256 cells and cells treated with bovine pancreas-derived RNase A (in the absence of NaCl and in the presence of 0.3 M NaCl);

FIG. 17 is a graph showing the results of a test of promotion of interleukin 12 production in peritoneal exudate macrophage cells by *Leuconostoc pseudomesenteroides* strain ATCC 12291 cells and cells treated with bovine pancreas-derived RNase A (in the absence of NaCl and in the presence of 0.3 M NaCl);

FIG. 18 is a graph showing the results of a test of promotion of interleukin 12 production in peritoneal exudate macrophage cells by bacteria cells of an isolate isolated from a commercially available drink, Yakult (Yakult Honsha), and cells treated with bovine pancreas-derived RNase A (in the absence of NaCl and in the presence of 0.3 M NaCl);

FIG. 19 is a graph showing the results of a test of promotion of interleukin 12 production in peritoneal exudate macrophage cells by bacteria cells of an isolate isolated from a commercially available plant-derived lactic acid bacteria drink, Labre (Kagome), and cells treated with bovine pancreas-derived RNase A (in the absence of NaCl and in the presence of 0.3 M NaCl);

FIG. 20 is a graph showing the results of a test of promotion of interleukin 12 production by various lactic acid bacteria in bone marrow-derived dendritic cells of TLR3-knockout mice;

FIG. 21 is a graph showing the results of promotion of interferon β by various lactic acid bacteria in bone marrow-derived dendritic cells of TLR3-knockout mice;

FIG. 22 is a graph showing the results of promotion of interleukin 12 production by *Tetragenococcus halophilus* strain Th221 cells in the presence of a TRIF pathway inhibitor;

FIG. 23 is a graph showing the results of a test of promotion of interleukin 12 production by *Tetragenococcus halophilus* strain NBRC 12172 cells in the presence of a TRIF pathway inhibitor;

FIG. 24 is a graph showing the results of a test of promotion of interleukin 12 production by *Tetragenococcus halophilus* strain Th221 cells in bone marrow-derived dendritic cells of TRIF-knockout mice;

FIG. 25 is a graph showing the results of measuring the expressed amount of TLR3 mRNA by real-time RT-PCR;

FIG. 26 shows the results of stimulating bone marrow-derived dendritic cells with *Tetragenococcus halophilus* strain Th221 cells prepared at different salt concentrations and analyzing the activation state of the dendritic cells at that time with Cell Quest software (BD Pharmingen) by respectively detecting markers CD40, CD80 and CD86 with FACS Calibur (BD Pharmingen) using PE-labeled anti-CD40 antibody (BD Pharmingen), PE-labeled anti-CD80 antibody (BD Pharmingen) and PE-labeled anti-CD86 antibody (BD Pharmingen);

FIG. 27 shows the results of purifying double-stranded RNA fractions from *Tetragenococcus halophilus* strain Th221 cells cultured under conditions of varying salt concentrations, and analyzing the content of double-stranded RNA by carrying out agarose gel electrophoresis of the double-stranded RNA fractions;

FIG. 28 is a graph showing the results of measuring interleukin 12 production promoting activity of purified double-stranded RNA fractions;

FIG. 29 is a graph showing the results of measuring interferon β production promoting activity of purified double-stranded RNA fractions;

FIG. 30 is a graph showing the results of measuring interferon β production promoting activity of bone marrow-derived dendritic cells induced by synthetic double-stranded RNA DSR1;

FIG. 31 is a graph showing the results of measuring interferon β production promoting activity of synthetic double-stranded RNA DSR1 in bone marrow-derived dendritic cells of TLR3-knockout mice;

FIG. 32 is a graph showing the results of measuring production of interferon β from bone marrow-derived dendritic cells attributable to differences in the sequence and length of synthetic double-stranded RNA;

FIG. 33 is a graph showing the results of measuring interferon β production from bone marrow-derived dendritic cells induced by synthetic double-stranded RNA DSR2; and, FIG. 34 shows the results of measuring the ratio of interferon γ-producing cells and interleukin 4-producing cells using FACS Aria flow cytometry (BD) when RNase-treated and non-RNase-treated lactic acid bacteria were added to bone marrow-derived dendritic cells and CD4+ T cells and co-cultured.

BEST MODE FOR CARRYING OUT THE INVENTION

The following provides a detailed explanation of the present invention.

(1) Double-Stranded RNA Derived from Lactic Acid Bacteria

The body's immune system plays an important role in defending against infections caused by microorganisms such as bacteria, yeast, molds and viruses, against tumors and in the onset of allergies, and the core of that defense mechanism are lymphocytes and antigen-presenting cells. Lymphocytes and antigen-presenting cells are activated antigen-specifically or antigen-non-specifically, and enhance the body's ability to eliminate foreign bodies.

During the activation of lymphocytes and antigen-presenting cells, interleukin 12 is known to activate antigen-presenting cells by acting on NK cells and T cells to induce production of interferon γ and tumor necrosis factor α, enhance the cytotoxic activity of NK cells and $CD8^+$ T cells, activate cytotoxic lymphocytes together with inducing lymphokine-activated killer cells by acting synergistically with interleukin 2, and be involved in differentiation of helper T cells assisting in cellular immunity (Th0) into Th1 T cells as well as control of the balance thereof (Th1/Th2 balance).

In this manner, interleukin 12 plays an important role enhancing immunoactivation activity such as defense against infections or antitumor activity, as well as preventing allergies, by enhancing both innate immunity and cellular immunity.

In the present invention, immunoregulatory action refers to activity that activates immune cells or antiallergic activity. This immunoregulatory action can be evaluated based on activity that promotes production of interleukin 12 from antigen-presenting cells.

Interleukin 12 production promoting activity can be easily assessed by culturing cells containing antigen-presenting cells, such as mouse peritoneal exudate macrophages, mouse suspended spleen cells or bone marrow-derived dendritic cells, on a tissue culture plate, adding a substance containing double-stranded RNA derived from lactic acid bacteria, culturing for a fixed period of time and then measuring the concentration of interleukin 12 in the medium by enzyme immunoassay.

Lactic acid bacteria refer to gram-positive bacteria in the form of bacilli or cocci. These bacteria are catalase-negative, produce 50% or more of lactic acid from consumed glucose, and do not form endospores. These bacteria may also rarely be motile. More specifically, these bacteria include genus *Tetragenococcus*, genus *Pediococcus*, genus *Lactobacillus*, genus *Streptococcus* and genus *Leuconostoc*.

Double-stranded RNA refers that in which a ribonucleotide and a ribonucleotide complementary thereto form a base pair. The presence of double-stranded RNA having immunoregulatory action can be verified by confirming (a) and (b) below.

(a) The immunoregulatory action of lactic acid bacteria cells is confirmed to decrease due to the action of bovine pancreas-derived RNase A. This makes it possible to verify the presence of an RNA fraction (single-stranded RNA and double-stranded RNA) and that this fraction has immunoregulatory action.

(b) TLR3 recognizing double-stranded RNA, and not TLR7 recognizing single-stranded RNA, is confirmed to be required for immunoregulatory action.

As an example of such a method, immunoregulatory action may be evaluated by using TLR7-deficient cells and TLR3-deficient cells, and confirming the presence of a decrease in activity in the TLR3-deficient cells as compared with the case of using normal cells.

Here, as an alternative to (b), (c) in the case of allowing bovine pancreas-derived RNase A to act in the presence of NaCl at 0.3 M or higher, immune activity may be confirmed to be higher than in the case of allowing to act in the absence of NaCl by using differences in sensitivity to bovine pancreas-derived RNase A. This is because bovine pancreas-derived RNase A only degrades single-stranded RNA, but does not degrade double-stranded RNA, in the presence of NaCl at a concentration of 0.3 M or higher.

The double-stranded RNA derived from lactic acid bacteria of the present invention is produced within bacteria cells as a result of culturing the lactic acid bacteria.

Examples of lactic acid bacteria include bacteria belonging to the genera *Tetragenococcus, Pediococcus, Lactobacillus, Streptococcus* and *Leuconostoc*, while specific examples include *Tetragenococcus halophilus* strain Th221, *Tetragenococcus halophilus* strain NBRC 12172, *Pediococcus pentosaceus* strain OS (NITE P-354), *Pediococcus pentosaceus* strain NRIC 1915, *Pediococcus pentosaceus* strain NRIC 0099, *Pediococcus pentosaceus* strain NRIC 0122, *Lactobacillus plantarum* strain NRIC 1930, *Lactobacillus plantarum* strain NRIC 1067, *Lactobacillus delbrueckii* subspecies *bulgaricus* strain NRIC 1688, *Lactobacillus delbrueckii* subspecies *lactis* strain NRIC 1683, *Lactobacillus brevis* strain NRIC 1713, *Lactobacillus pentosus* strain NRIC 0391, *Lactobacillus pentosus* strain NRIC 0396, *Lactobacillus pentosus* strain NRIC 1836, *Lactobacillus casei* subspecies *casei* strain NRIC 0644, *Lactobacillus paracasei* subspecies *paracasei* strain NRIC 1936, *Streptococcus thermophilus* strain NRIC 0256, *Leuconostoc mesenteroides* subspecies *mesenteroides* strain NRIC 1982, *Leuconostoc pseudomesenteroides* strain ATCC 12291 and *Leuconostoc lactis* strain NRIC 1582.

Furthermore, one example of the present invention in the form of *Tetragenococcus halophilus* strain Th221 is deposited at the International Patent Organism Depositary, National Institute of Advanced Industrial Science and Technology under the accession number FERM AP-21310.

The aforementioned lactic acid bacteria can be used by isolating from soy sauce moromi mash, pickled vegetables, commercially available lactic acid bacteria drinks and the like. The lactic acid bacteria may be cultured in any manner provided bacteria cells thereof produce double-stranded RNA.

Numerous factors are known to be involved in the signal transduction pathways involved in immunoregulatory action.

Signals generated by TLR following recognition of a constituent component such as bacteria are converted within cells mediated by adapter molecules such as MyD88, TRIF or TIRAP, and activate NF-kB and MAPK downstream.

Thus, in the case immunoregulatory action decreases in cells lacking TLR3, it means that the signal transduction pathway dependent on that adapter molecule TRIF is involved in immunoregulatory action. In addition, in order to verify that a signal transduction pathway is dependent upon MyD88, immunoregulatory action ought to demonstrate a decrease in the case of evaluating using cells lacking MyD88.

In the case of ingesting double-stranded RNA derived from lactic acid bacteria for the purpose of immunoregulation, the amount ingested may be suitably set according to the symptoms and physique of the ingesting person. Double-stranded RNA derived from lactic acid bacteria can be administered directly in the form of lactic acid bacteria cells, or purified double-stranded RNA derived from lactic acid bacteria can be administered to the body by incorporating in liposomes.

In the case of ingesting double-stranded RNA contained in the cells of lactic acid bacteria belonging to the genera *Tetragenococcus, Pediococcus, Lactobacillus, Streptococcus* or *Leuconostoc*, the ingested amount of lactic acid bacteria cells is, for example, 1 to 1000 mg/60 kg of body weight/day.

Double-stranded RNA derived from lactic acid bacteria having activity that activates immune cells may be used alone or may be used by adding to a food, drink or pharmaceutical.

(2) Production Process of Lactic Acid Bacteria-Derived Double-Stranded RNA

The double-stranded RNA derived from lactic acid bacteria of the present invention can be produced within bacteria cells by culturing lactic acid bacteria. For example, the lactic acid bacteria-derived double-stranded RNA is obtained by culturing one strain or two or more strains of lactic acid bacteria selected from genus *Tetragenococcus*, genus *Pediococcus*, genus *Lactobacillus*, genus *Streptococcus* and genus *Leuconostoc* followed by collecting culture, cells or cell components containing double-stranded RNA.

Although there are no particular limitations on the lactic acid bacteria medium or culturing conditions provided the bacteria cells produce double-stranded RNA, larger amounts of double-stranded RNA can be produced within cells by culturing lactic acid bacteria under stressful conditions. Here, stressful conditions refer to stress resulting from a high salt concentration, high temperature, low nutrient levels, low pH and the like.

In the case of lactic acid bacteria belonging to the genus *Tetragenococcus* in particular, culturing is preferably carried out using medium having a salt content of 0.5 to 25% and preferably 5 to 10%. Lactic acid bacteria belonging to the genus *Tetragenococcus* proliferate extremely slowly in medium having a salt concentration of 0.5% or less or 25% or more, thereby making this impractical.

Although lactic acid bacteria cultures, lactic acid bacteria cells or lactic acid bacteria cell components containing double-stranded RNA derived from lactic acid bacteria can be used as is, the double-stranded RNA derived from lactic acid bacteria may also be concentrated and purified. In the case of concentrating and purifying double-stranded RNA derived from lactic acid bacteria, concentration and purification may be carried out in the manner described below.

First, a nucleic acid fraction is extracted from heat-treated lactic acid bacteria cells in accordance with a known method. For example, the cells may be physically crushed using glass beads and the like, or may be lysed by using a bacteriolytic enzyme on lactic acid bacteria cells, followed by treating with phenol-chloroform. Subsequently, the cells can be purified using, for example, cellulose column chromatography or differences in sensitivity to bovine pancreas-derived RNase A.

For example, after adsorbing the extracted nucleic acid to cellulose in the presence of ethanol and washing, a fraction in which double-stranded RNA derived from lactic acid bacteria has concentrated is eluted with a buffer not containing ethanol. Double-stranded RNA derived from lactic acid bacteria can then be purified by carrying out DNase treatment, and by bovine pancreas-derived RNase A treatment under conditions such that only single-stranded RNA is cleaved (such as in the presence of 0.3 M NaCl), on this fraction.

The following indicates an example of a process for producing double-stranded RNA derived from lactic acid bacteria belonging to the genus *Tetragenococcus, Pediococcus, Lactobacillus, Streptococcus* or *Leuconostoc*.

*Tetragenococcus* species are cultured in MRS medium (BD) containing 0.5 to 25% salt and preferably 5 to 10% salt, while *Pediococcus* species, *Lactobacillus* species, *Streptococcus species* and *Leuconostoc* species are cultured in ordinary MRS medium, for 24 to 72 hours at 25 to 37° C. Lactic acid bacteria cultures and lactic acid bacteria cells obtained in this manner contain double-stranded RNA, and can be efficiently incorporated into cells without requiring special treatment such as incorporating in liposomes.

Purification of double-stranded RNA from a lactic acid bacteria culture or lactic acid bacteria cells is carried out, for example, in the manner indicated below. After heat-killing a lactic acid bacteria culture or lactic acid bacteria cells, the lactic acid bacteria cells are washed and suspended in a buffer solution followed by adding lysozyme and warming at 37° C. Subsequently, SDS and Proteinase K are added followed by warming at 37° C. Subsequently, treatment with phenol, chloroform and isoamyl alcohol is carried out to obtain a supernatant. The crude nucleic acid extract obtained here is a mixture containing DNA, single-stranded RNA and double-stranded RNA.

Next, double-stranded RNA derived from lactic acid bacteria is purified by cellulose column chromatography. Ethanol is added to the crude nucleic acid extract to a final concentration of 15%. Cellulose powder is then added to this solution to a final concentration of 5%, and the double-stranded RNA is adsorbed to the cellulose powder.

CF11 Cellulose Powder (Wattman) is preferably used for the cellulose powder. The double-stranded RNA is more strongly adsorbed to the cellulose powder than DNA and single-stranded RNA in the presence of 15% ethanol. Cellulose powder to which double-stranded RNA had adsorbed can be recovered in the form of a precipitate by centrifugal separation.

The recovered cellulose is then re-suspended in a buffer solution containing 15% ethanol, for example, followed by pouring the suspension into the column. Buffer solution containing 15% ethanol is then passed through the column, while adsorbed components other than double-stranded RNA derived from lactic acid period are washed out.

The double-stranded RNA derived from lactic acid bacteria adsorbed on the cellulose column can be recovered by passing a buffer solution not containing ethanol through the column. Double-stranded RNA derived from lactic acid bacteria can then be obtained by carrying out alcohol precipitation treatment on the liquid sample resulting from the aforementioned treatment.

Since DNA and single-stranded RNA also present in the crude nucleic acid extract cannot be completely removed by the aforementioned cellulose column chromatography, it is preferable to carry out an even higher degree of purification. Residual DNA can be degraded and removed using, for example, a DNA degrading enzyme in the form of DNase I (Takara Shuzo). In addition, residual single-stranded RNA can be degraded and removed using an RNA degrading enzyme such as bovine pancreas-derived RNase A (Sigma) in the presence of NaCl at a concentration of 0.3 M or more. Subsequently, purified lactic acid bacteria-derived double-stranded RNA can be obtained by carrying out phenol/chloroform extraction and alcohol precipitation.

The purified lactic acid bacteria-derived double-stranded RNA can be administered to the body by incorporating in liposomes.

Although the following provides a more detailed explanation of the present invention through examples thereof, the present invention is not limited to these examples.

EXAMPLE 1

Test of Promotion of Interleukin 12 Production by *Tetragenococcus halophilus* Strain Th221 Cells Treated with Bovine Pancreas-Derived RNase A Heat-killed *Tetragenococcus halophilus* strain Th221 cells were treated with bovine pancreas-derived RNase A followed by an evaluation of the interleukin 12 production promoting activity of a cell suspension using mouse peritoneal exudate macrophage cells and suspended spleen cells.

(1) Preparation of Lactic Acid Bacteria Suspensions

The lactic acid bacteria *Tetragenococcus halophilus* strain Th221 were inoculated into MRS medium containing 0.5%, 5% or 10% salt at $1 \times 10^7$ cells/ml. Following stationary culturing for 48 to 72 hours, heat killing was carried out by heating for 10 minutes at 95° C. Subsequently, the bacteria were collected by removing the media by centrifugation. After washing the cells with physiological saline, lactic acid bacteria suspensions were prepared by suspending in physiological saline at $1 \times 10^9$ cells/ml.

(2) Bovine Pancreas-Derived RNase A Treatment

Bovine pancreas-derived RNase A (Sigma) was added to the lactic acid bacteria suspension to a concentration of 10 µg/ml followed by incubating for 1 hour at 37° C. Subsequently, the cells were washed with physiological saline and again suspended in physiological saline at $1 \times 10^9$ cells/ml to prepare lactic acid bacteria suspensions.

(3) Collection and Preparation of Peritoneal Exudate Macrophage Cells

Peritoneal exudate macrophages were aseptically collected from mice (8-week-old BALB/c, females, acquired from Charles River Laboratories) stimulated by intraperitoneal administration of 2 ml of thioglycolate (BD) three days after administration. After measuring the number of cells in the peritoneal exudate macrophage cell suspension, the number of cells was adjusted to a concentration of $2 \times 10^6$ cells/ml with RPMI complete medium. The composition of the RPMI complete medium consisted of the addition of 10% inactivated fetal calf serum (FCS, Invitrogen) to RPMI-1640 (GIBCO) medium containing 25 mM HEPES, 100 µg/ml of penicillin, 100 µg/ml of streptomycin, 50 µM 2-mercaptoethanol and 2 mM L-glutamic acid. The adjusted peritoneal exudate macrophage cell liquid was inoculated into a 96-well tissue culture plate at 100 µl per well.

(4) Preparation of Spleen Cell Suspension

Six-week-old BALB/c mice (acquired from Japan SLC) were sacrificed by cervical dislocation under isoflurane inhalation anesthesia followed by excision of the spleen by laparotomy and placing in a 6 cm cell culturing dish containing ice-cooled RPMI 1640 medium containing 1% FCS. Two spleens were cut into thin sections with a scissors, placed in 50 ml plastic tubes (BD Falcon) with base medium containing collagenase at 400 U/ml (10 ml), and gently stirred with a stirrer for 30 minutes in an incubator (37° C.).

The base medium consisted of the addition of 10% FCS (Hyclone), inactivated for 30 minutes at 56° C., to RPMI-1640 medium (Gibco) containing penicillin (100,000 U/L, Meiji Seika), streptomycin (100 µg/L, Meiji Seika), 2-mercaptoethanol (50 µm, Gibco), L-glutamic acid (2 mM, Nacalai-Tesque) and HEPES (20 mM, Dojin Chemical). The resulting cell suspension was centrifuged for 5 minutes at 440×g followed by washing twice with RPMI 1640 medium containing 1% FCS.

After suspending the cells in RPMI 1640 medium containing 1% FCS, the suspension was filtered with a cell strainer, and the remaining cell masses were filtered by crushing with the plunger of a 10 ml plastic syringe (Terumo).

The resulting cell suspension was centrifuged followed by removal of the supernatant by aspiration, adding 5 ml of hemolysis buffer (0.155 M $NH_4Cl$, 0.01 M Tris, pH 7.5), gently suspending by adding FCS (5 ml) after allowing to stand on ice for 5 minutes, adding RPMI 1640 medium containing 1% FCS (10 ml) and centrifuging for 7 minutes at 400×g. After further washing three times with RPMI 1640 medium containing 1% FCS, the cells were suspended in base medium. The number of cells in the cell liquid was measured with a hemocytometer. The prepared suspended spleen cells were inoculated into a 96-well plate at $5.0 \times 10^5$ cells/0.2 ml/well.

(5) Measurement of Interleukin 12 Production Promoting Activity

The two types of cell suspensions obtained as described above and lactic acid bacteria suspensions before and after treatment with bovine pancreas-derived RNase A were mixed so that the ratio of the number of cells to the number of lactic acid bacteria was 1:50 followed by co-culturing for 24 hours in a 5% $CO_2$ incubator at 37° C. The supernatant was then recovered and the concentration of interleukin 12 was measured by enzyme immunoassay.

Enzyme immunoassay was carried out by adding 100 µl of a solution of rat anti-mouse interleukin 12 antibody (Pharmingen) adjusted to 2 µg/ml with 0.2 M, pH 6.0 phosphate buffer to each well of a 96-well tissue culture plate, and allowing to stand overnight at room temperature to allow the rat anti-mouse interleukin 12 antibody to adhere to the each well.

Culture supernatant was then added at 100 µl/well followed by allowing to stand for 90 minutes at room temperature to allow the mouse interleukin 12 in the culture supernatant to bind to the rat anti-mouse interleukin 12 antibody adhered to the plate. After washing the plate, rat biotinated anti-mouse interleukin 12 antibody (Pharmingen) was added to bind to the mouse interleukin 12.

After washing the plate, streptoavidin-labeled peroxidase enzyme (Vector) was added and bound to the biotin.

After washing the plate, TMB substrate solution (Moss/Cosmo Bio) was then added at 100 µl per well and allowed to react for 20 minutes at room temperature. After stopping the reaction with 0.5 N hydrochloric acid, absorbance at 450 nm was measured with a microplate reader, and the concentration of interleukin 12 in the culture supernatant was determined from a calibration curve prepared with recombinant mouse interleukin 12 (Pharmingen).

Figure 1:
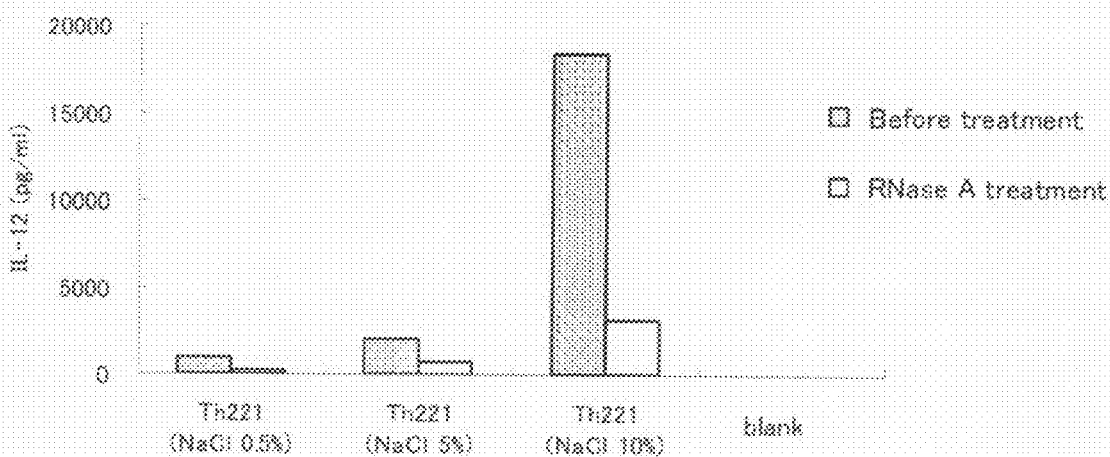
FIG. 1 is a graph showing the results of a test of promotion of interleukin 12 production in peritoneal exudate macrophage cells by *Tetragenococcus halophilus* strain Th221 cells and cells treated with bovine pancreas-derived RNase A.
Figure 2:
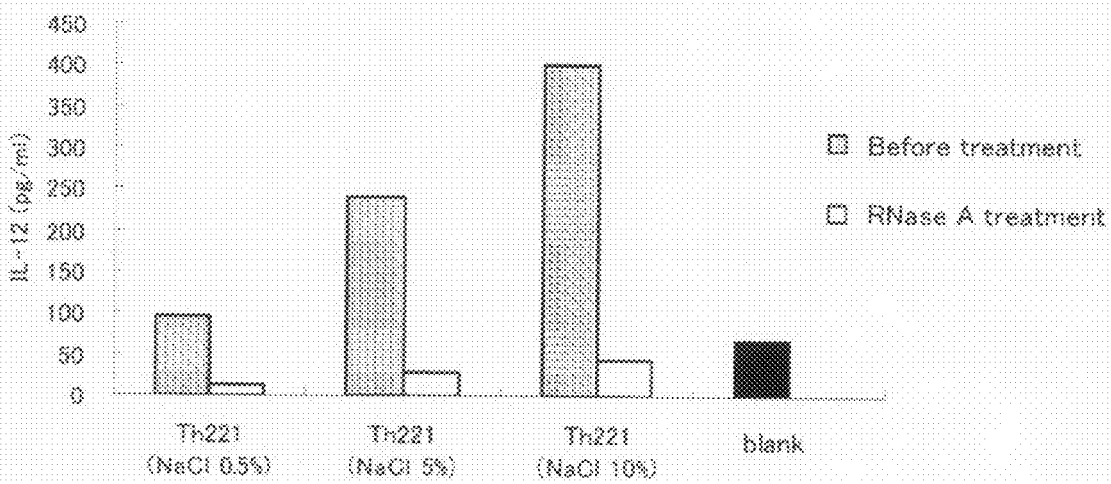
FIG. 2 is a graph showing the results of a test of promotion of interleukin 12 production in suspended spleen cells by *Tetragenococcus halophilus* strain Th221 cells and cells treated bovine pancreas-derived RNase A.

The results in the case of using peritoneal exudate macrophage cells are shown in FIG. 1, while the results in the case of using suspended spleen cells are shown in FIG. 2. In both cases, immunoregulatory action of the bacteria cells decreased when bovine pancreas-derived RNase A was allowed to act on the cells. As a result, it was shown that there exists the RNA fraction (single-stranded RNA and double-stranded RNA) and that this fraction was indicated to have immunoregulatory action.

In addition, in the case of using either of the cells, the decrease in immunoregulatory action was greater in bacteria cells for which there was a high salt concentration in the medium during culturing. On the basis thereof, the amount of RNA fragment having immunoregulatory action was determined to be greater for higher concentrations of salt in the medium during culturing.

EXAMPLE 2

Test of Promotion of Interleukin 12 Production by *Tetragenococcus halophilus* Strain Th221 Cells in Bone Marrow-Derived Dendritic Cells of TLR3-, TLR7- and MyD88-Knockout Mice Bone marrow-derived dendritic cells were prepared from mice in which TLR3, recognizing double-stranded RNA, TLR7, recognizing single-stranded RNA, and MyD88, which is an adapter molecule of the signal transduction pathway involved in immunoregulatory action, had been knocked out followed by measurement of interleukin 12 production promoting activity.

(1) Preparation of Lactic Acid Bacteria Suspensions

The lactic acid bacteria *Tetragenococcus halophilus* strain Th221 were inoculated into MRS medium containing 0.5%, 5% or 10% salt at $1 \times 10^7$ cells/ml. Following stationary culturing for 48 to 72 hours, heat killing was carried out by heating for 10 minutes at 95° C. Subsequently, the bacteria were collected by removing the media with a centrifugal concentrator. After washing the cells with physiological saline, lactic acid bacteria suspensions were prepared by suspending in physiological saline at $1 \times 10^9$ cells/ml.

(2) Preparation of Bone Marrow-Derived Dendritic Cells

The test was carried out using wild type mice and mice in which TLR3, TLR7 and MyD88 had been knocked out (6 to 12-week old C57BL/6 mice, females, acquired from the Hyogo College of Medicine). After sacrificing the animals by cervical dislocation under isoflurane inhalation anesthesia, the femur and tibia were removed from the legs and placed in a 6 cm cell culture tissue dish containing ice-cooled RPMI-1640 medium (Sigma) containing 1% fetal calf serum (FCS, inactivated). The bone marrow was suspended after evacuating by injecting RPMI-1640 medium containing 1% FCS.

The resulting cell suspension was filtered with a cell strainer (40 µm, BD Falcon) followed by centrifuging for 5 minutes at 440×g.

After adding hemolysis buffer (5 mL, 0.155 M $NH_4Cl$, 0.01 M Tris, pH 7.5) and allowing to stand for 5 minutes on ice, RPMI-1640 medium containing 1% FCS (5 mL) was added followed by centrifuging and washing twice with RPMI-1640 medium containing 1% FCS.

An antibody cocktail (100 µL/$10^7$ cells) consisting of phycoerythrin (PE)-labeled I-A antibody (Clone M5/144.14.2, BD Pharmingen, 0.2 mg/mL), PE-labeled anti-CD4 antibody (Clone GK1.5, BD Pharmingen, 0.2 mg/mL) and PE-labeled anti-CD8 antibody (Clone 53-6.7, BD Pharmingen, 0.2 mg/mL) each diluted 1000-fold with MACS running buffer, and rabbit IgG (50 µg/mL, Zymed), were added followed by allowing to stand undisturbed for 30 minutes on ice.

After washing once with the MACS running buffer, anti-PE magnetic beads (20 µL/$10^7$ cells, Miltenyi) and MACS running buffer (80 µL/$10^7$ cells) were added followed by allowing to stand undisturbed for 15 minutes at 4 to 8° C.

After washing once with MACS running buffer equal to 20 times the amount of reaction solution, the cells were suspended in MACS running buffer (0.5 mL/$10^8$ cells) followed by separation of the negative fraction using an automatic magnetic separation system (Auto MACS, Miltenyi).

The isolated cells were washed once with RPMI-1640 medium containing 1% FCS followed by suspending in a base medium containing granulocyte/macrophage colony stimulating factor (GM-CSF).

The base medium consisted of the addition of 10% FCS, (Hyclone), inactivated for 30 minutes at 56° C., to RPMI-1640 medium (Gibco) containing penicillin (100,000 U/L, Meiji Seika), streptomycin (100 µg/L, Meiji Seika), 2-mercaptoethanol (50 µM, Gibco), L-glutamic acid (2 mM, Nacalai-Tesque) and HEPES (20 mM, Dojin Chemical).

GM-CSF consisted of the addition of a culture supernatant of plasmocytoma X63-Ag8 inserted with mouse GM-CSF gene (J558L-GM-CSF) to the base medium at 10%. The cell liquid was suspended in Trypan blue (Gibco), and after measuring the number of cells using a hemocytometer, the cell liquid was dispensed into a 6-well cell culturing plate (BD Falcon) to $1.2 \times 10^6$ cells/4 mL/well) and cultured.

2 mL of medium were removed by aspiration on day 3 and day 6 after the start of culturing followed by the addition of 2 mL of base medium containing GM-CSF and recovering the suspended cells on day 8 after the start of culturing in the form of immature dendritic cells (CD11c-positive cells: >95%). After washing the cells three times with RPMI-1640 medium containing 1% FCS, the cells were suspended in base medium to obtain bone marrow-derived dendritic cell suspensions.

(3) Measurement of Interleukin 12 Production Promoting Activity

Figure 3:
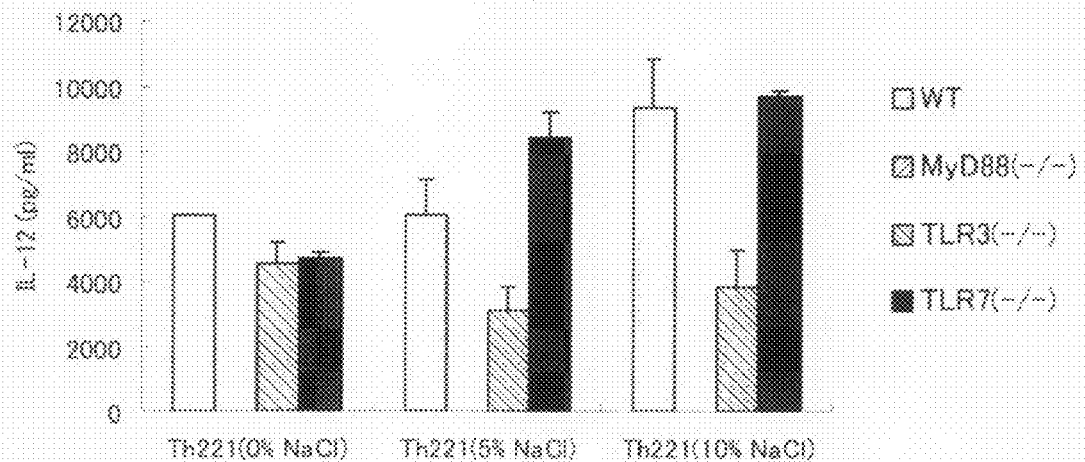
FIG. 3 is a graph showing the results of a test of promotion of interleukin 12 production in bone marrow-derived dendritic cells of knockout mice by *Tetragenococcus halophilus* strain Th221 cells.

Measurement was carried out in the same manner as Example 1. The results are shown in FIG. 3.

Although interleukin 12 production promoting activity decreased in bone marrow-derived dendritic cells obtained from TLR3-knockout mice, there was no change in activity in bone marrow-derived dendritic cells obtained from TLR7-knockout mice. On the basis thereof, the RNA fraction having immunoregulatory action was indicated to be a TLR3 ligand in the form of double-stranded RNA and not a TLR7 ligand in the form of single-stranded RNA.

In addition, since activity decreased in bone marrow-derived dendritic cells obtained from TLR3-knockout mice, the signal transduction pathway dependent on the TLR3 adapter molecule TRIF was shown to be related to immunoregulatory action.

Interleukin 12 production promoting activity disappeared in bone marrow-derived dendritic cells obtained from MyD88-knockout mice.

On the basis of these findings, a TRIF-dependent signal transduction pathway and an MyD88-dependent signal transduction pathway were shown to be acting in coordination with the immunoregulatory action demonstrated by *Tetragenococcus halophilus* strain Th221 containing double-stranded RNA.

EXAMPLE 3

Test of Promotion of Interleukin 12 Production by *Tetragenococcus halophilus* Strain Th221 Cells Treated with Bovine Pancreas-Derived RNase A Under Conditions Causing Cleavage of Single-Stranded RNA Only (0.3 M NaCl)

The production of double-stranded RNA having immunoregulatory action was confirmed in *Tetragenococcus halophilus* strain Th221 cells by using differences in sensitivity to bovine pancreas-derived RNase A.

(1) Preparation of Lactic Acid Bacteria Suspensions

*Tetragenococcus halophilus* strain Th221 were inoculated into MRS medium containing 10% salt at $1 \times 10^6$ cells/ml. Following stationary culturing for 72 hours, heat killing was carried out by heating for 10 minutes at 95° C. Two fractions were collected from the samples, and after washing one of the fractions with 10 mM Tris-HCl (pH 8.0) and the other with 10 mM Tris-HCl (pH 8.0) containing 0.3 M NaCl, the bacteria cells were suspended in each of the liquids. The suspensions were adjusted to an $OD_{600nm}$ value of 10.

(2) Bovine Pancreas-Derived RNase A Treatment

Bovine pancreas-derived RNase A (Sigma) was added to the above lactic acid bacteria suspensions to a concentration of 10 µg/ml followed by incubating for 2 hours at 37° C. In this enzyme treatment, both single-stranded RNA and double-stranded RNA are degraded in the absence of NaCl, while only single-stranded RNA is degraded in the presence of 0.3 M NaCl. Following enzyme treatment, the bacteria cells were respectively washed twice with 10 mM Tris-HCl (pH 8.0) and 10 mM Tris-HCl (pH 8.0) containing 0.3 M NaCl followed by suspending in RPMI complete medium. The suspensions were adjusted to an $OD_{600nm}$ value of 0.125.

(3) Collection and Preparation of Peritoneal Exudate Macrophage Cells

Collection and preparation were carried out in the same manner as Example 1.

(4) Measurement of Interleukin 12 Production Promoting Activity

Measurement was carried out in the same manner as Example 1.

Figure 4:
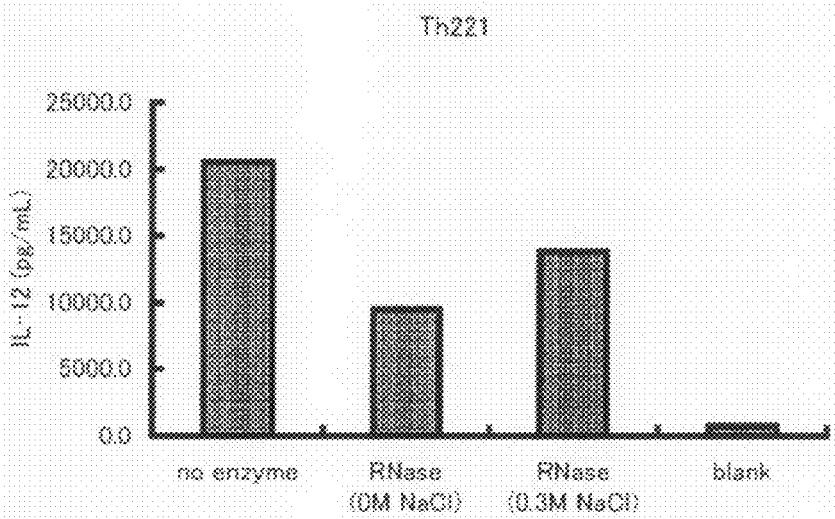
FIG. 4 is a graph showing the results of a test of promotion of interleukin 12 production in peritoneal exudate macrophage cells by *Tetragenococcus halophilus* strain Th221 cells and cells treated with bovine pancreas-derived RNase A (in the absence of NaCl and in the presence of 0.3 M NaCl)

The results are shown in FIG. 4. Although interleukin 12 production promoting activity decreased considerably in the sample that underwent enzyme treatment in the absence of NaCl, the decrease in interleukin 12 production promoting activity was small in the sample that underwent enzyme treatment in the presence of 0.3 M NaCl. Thus, the double-stranded RNA fraction was indicated to have interleukin 12 production promoting activity.

(5) Confirmation of Degradation of RNA in Bacteria Cells

Degradation of RNA in bacteria cells resulting from treatment of heat-sterilized lactic acid bacteria suspensions with RNase A was confirmed in the manner described below.

Samples (1) to (3) consisting of: (1) heat-killed lactic acid bacteria, (2) lactic acid bacteria treated with RNase A in the presence of 10 mM Tris-HCl (pH 8.0)-following heat treatment, and (3) lactic acid bacteria treated with RNase A in the presence of 10 mM Tris-HCl (pH 8.0) containing 0.3 M NaCl following heat treatment, were respectively suspended in 2.5 ml of STE buffer (100 mM NaCl, 10 mM Tris-HCl, 1 mM EDTA (pH 8.0)). 0.25 ml of 50 mg/ml lysozyme were then added thereto followed by incubating for 30 minutes at 37° C.

Subsequently, 50 µl of STE buffer, 0.15 ml of 10% SDS and 15 µA of 20 mg/ml Proteinase K were added followed by incubating for 1 hour at 37° C. 3 ml of a mixture of chloroform and isoamyl alcohol were then added thereto followed by mixing, centrifuging and recovering the supernatant.

Subsequently, an equal volume of a mixture of phenol, chloroform and isoamyl alcohol was added followed by mixing, centrifuging and recovering the supernatant. This procedure was carried out twice. After adding 0.6 equivalents of isopropanol and precipitating, the precipitate was suspended in 5 ml of TRIzol (Invitrogen). 1 ml of chloroform was then added followed by mixing, centrifuging and recovering the supernatant. Subsequently, after adding 2.5 ml of isopropanol and allowing to stand for 10 minutes, the mixture was centrifuged and the precipitate was recovered to obtain RNA fractions. The RNA fractions were electrophoresed in agarose gel.

Figure 5:
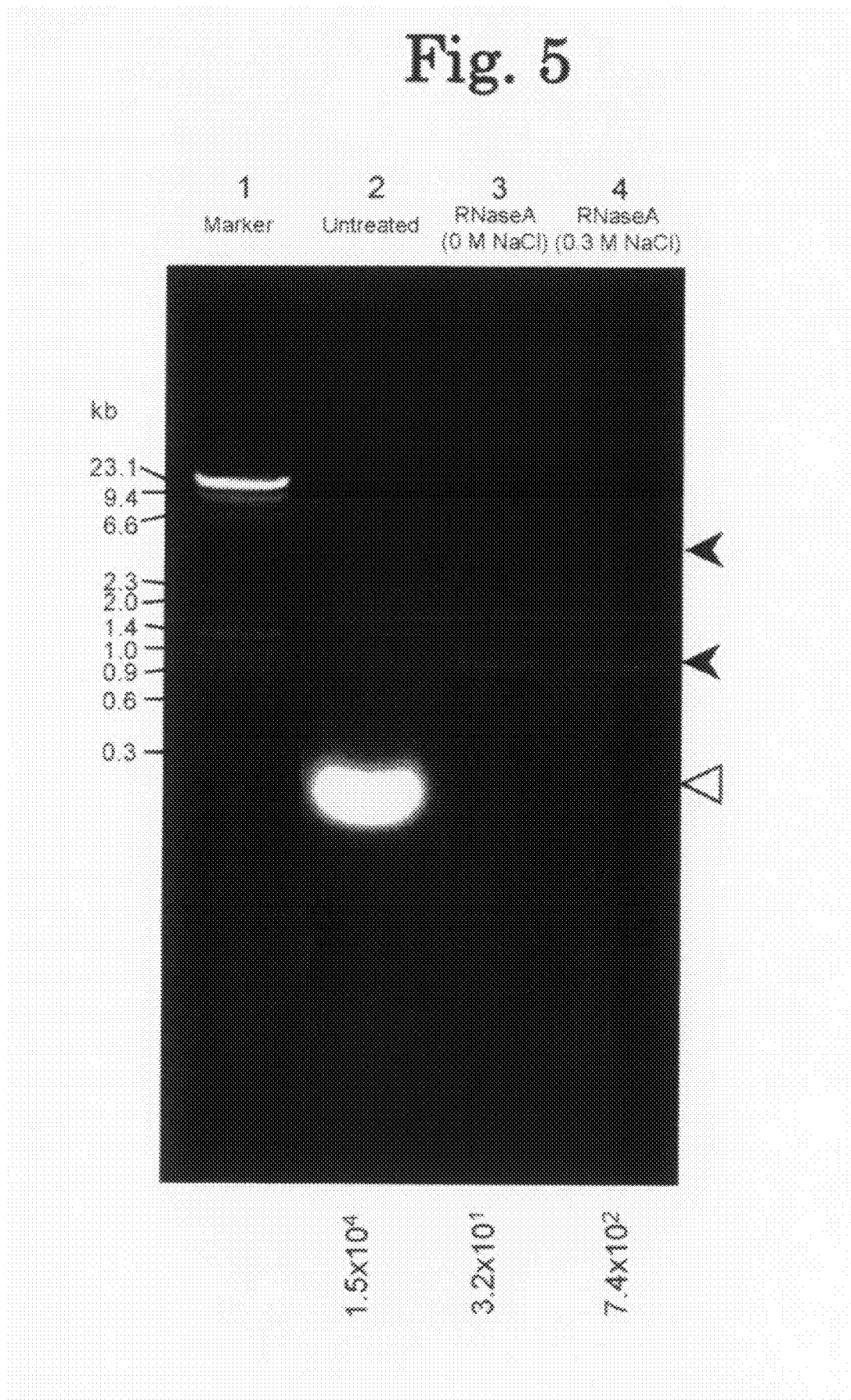
FIG. 5 shows the results of agarose gel electrophoresis of RNA fragments obtained by treating heat-killed lactic acid bacteria suspensions with bovine pancreas-derived RNase A (under conditions of 0 M NaCl and 0.3 M NaCl) and purifying RNA fractions from the bacteria cells; wherein, the results of measuring low molecular weight RNA fractions with a densitometer are indicated with the values shown below each lane, the white triangular pointer indicates the low molecular weight RNA fraction, and the black triangular pointers indicate plasmid DNA retaining strain Th221 unable to be completely removed with TRIzol treatment.

The results are shown in FIG. 5. The RNA was present mainly in a low molecular weight state (white triangular pointer). In addition, plasmid DNA retained by strain Th221 that was unable to be completely removed by TRIzol treatment was also detected (black triangular pointers). The values shown in FIG. 5 were obtained as a result of measuring the low molecular weight RNA fraction with a densitometer, and RNA within the bacteria cells was confirmed to be degraded by RNase A treatment of heat-killed lactic acid bacteria suspensions.

EXAMPLE 4

Test of Promotion of Interleukin 12 Production by *Tetragenococcus halophilus* Strain Th221 Cells Treated with S1 Nuclease Cleaving Single-Stranded Nucleic Acids The importance of a double-stranded structure for the structure of nucleic acids having immunoregulatory action in *Tetragenococcus halophilus* strain Th221 cells was confirmed by carrying out a test using treatment with S1 nuclease, which cleaves single-stranded nucleic acids, in addition to the test of Example 3 using differences in sensitivity to bovine pancreas-derived RNase A.

(1) Preparation of Lactic Acid Bacteria Suspensions

*Tetragenococcus halophilus* strain Th221 were inoculated into MRS medium containing 10% salt at $1 \times 10^6$ cells/ml. Following stationary culturing for 72 hours, heat killing was carried out by heating for 10 minutes at 95° C. The sample was divided into three fractions. After washing the first fraction with 10 mM Tris-HCl (pH 8.0), the second fraction with 10 mM Tris-HCl (pH 8.0) containing 0.3 M NaCl, and the third fraction with S1 nuclease buffer (30 mM sodium acetate pH 4.6, 280 mM NaCl, 1 mM $ZnSO_4$), the bacteria cells were suspended in each of the liquids. The suspensions were adjusted to an $OD_{600nm}$ value of 10.

(2) Bovine Pancreas-Derived RNase A Treatment and S1 Nuclease Treatment

Bovine pancreas-derived RNase A (Sigma) was added to the first fraction and the second fraction to a concentration of 10 µg/ml followed by incubating for 2 hours at 37° C. S1 nuclease (Takara Shuzo) was added to the third fraction to a concentration of 2000 U/ml. Following enzyme treatment, the fractions were washed twice with their respective enzyme treatment buffers and then suspended in RPMI complete medium. The suspensions were adjusted to an $OD_{600nm}$ value of 0.125.

(3) Collection and Preparation of Peritoneal Exudate Macrophage Cells and Preparation of Bone Marrow-Derived Dendritic Cells Collection and preparation were carried out in the same manner as Example 1. Preparation of bone marrow-derived dendritic cells was carried out in the same manner as Example 2.

(4) Measurement of Interleukin 12 Production Promoting Activity

Figure 6:
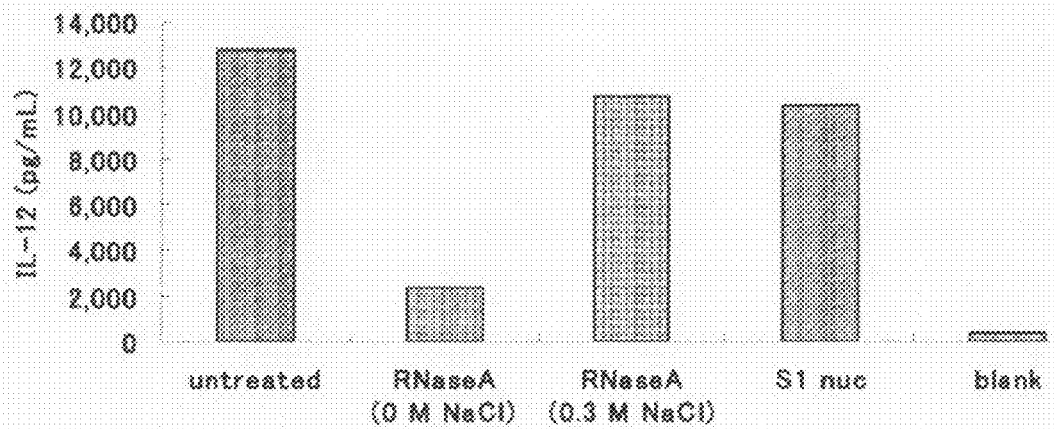
FIG. 6 is a graph showing the results of a test of promotion of interleukin 12 production from peritoneal exudate macrophage cells by *Tetragenococcus halophilus* strain Th221 cells treated with bovine pancreas-derived RNase A (under conditions of 0 M NaCl and 0.3 M NaCl) and S1 nuclease enzyme.

Measurement of activity promoting production of interleukin 12 from peritoneal exudate macrophage cells was carried out in the same manner as Example 1. The results are shown in FIG. 6. Although interleukin 12 production promoting activity decreased considerably in the sample treated with RNase A in the absence of NaCl, there were no decreases in interleukin 12 production promoting activity observed in the sample treated with RNase A in the presence of 0.3 M NaCl or in the sample treated with S1 nuclease.

Figure 7:
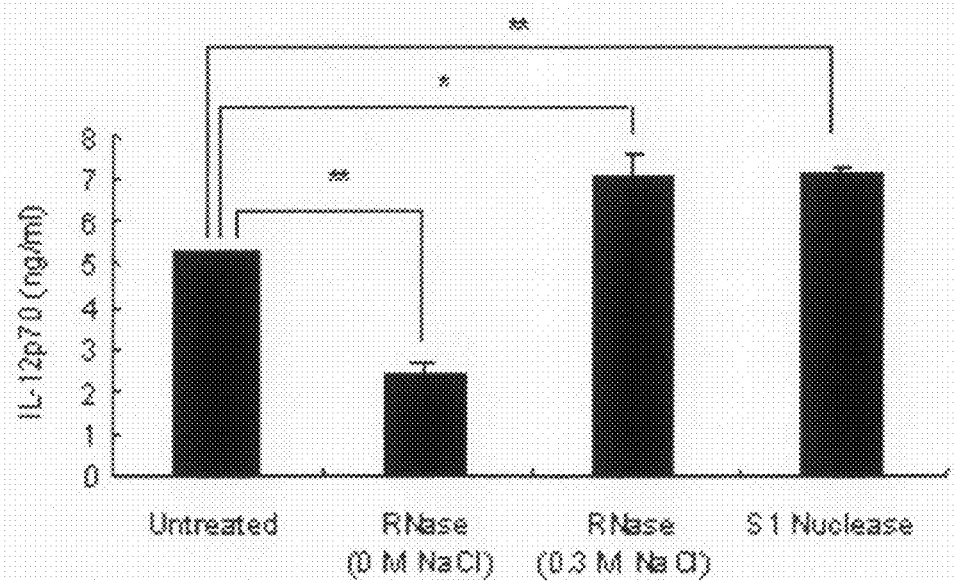
FIG. 7 is a graph showing the results of a test of promotion of interleukin 12 production from bone marrow-derived dendritic cells by *Tetragenococcus halophilus* strain Th221 cells treated with bovine pancreas-derived RNase A (under conditions of 0 M NaCl and 0.3 M NaCl) and S1 nuclease enzyme.

Measurement of activity promoting production of interleukin 12 from bone marrow-derived dendritic cells was carried out in the same manner as Example 2. The results are shown in FIG. 7. Although interleukin 12 production promoting activity decreased considerably in the same treated with RNase A in the absence of NaCl, there were no decreases in interleukin 12 production promoting activity observed in the sample treated with RNase A in the presence of 0.3 M NaCl or in the sample treated with S1 nuclease.

Figure 8:
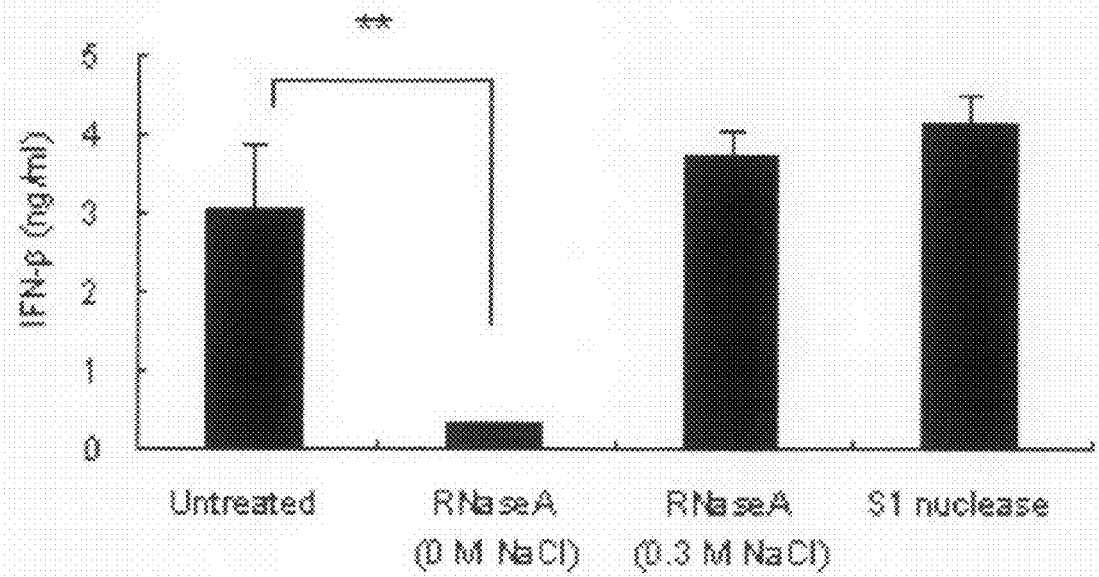
FIG. 8 is a graph showing the results of a test of promotion of interferon β production from bone marrow-derived dendritic cells by *Tetragenococcus halophilus* strain Th221 cells treated with bovine pancreas-derived RNase A (under conditions of 0 M NaCl and 0.3 M NaCl) and S1 nuclease enzyme.

In addition, measurement was also carried out on interferon β, which has been reported to be involved in the production of interleukin 12. Activity promoting production of interferon β from bone marrow-derived dendritic cells (after culturing for 6 hours using an interferon β assay kit (PBL)) was as shown in FIG. 8.

On the basis of these results, a double-stranded structure was confirmed to be important for the structure of nucleic acids having immunoregulatory action.

EXAMPLE 5

Production of Double-Stranded RNA in Various Lactic Acid Bacteria

The production of double-stranded RNA having immunoregulatory action was also confirmed in *Tetragenococcus halophilus* strain NBRC 12172, *Pediococcus pentosaceus* strain OS, *Pediococcus pentosaceus* strain NRIC 1915, *Lactobacillus delbrueckii* subspecies *bulgaricus* strain NRIC 1688, *Lactobacillus delbrueckii* subspecies *lactis* strain NRIC 1683, *Lactobacillus brevis* strain NRIC 1713, *Streptococcus thermophilus* strain NRIC 0256, *Leuconostoc pseudomesenteroides* strain ATCC 12291, isolated bacteria cells of a commercially available drink, Yakult (Yakult Honsha), and isolated bacteria cells of a plant-derived lactic acid bacteria drink, Labre (Kagome), using differences in sensitivity to bovine pancreas-derived RNase A.

Furthermore, the Yakult isolated strain was identified as genus *Lactobacillus*, species *paracasei*, subspecies *paracasei*, while the plant-derived lactic acid drink Labre isolated strain was identified as genus *Lactobacillus*, species *brevis* or genus *Lactobacillus*, species *collinoides* using the lactic acid bacteria identification kit API50CH (Biomerieux Japan).

(1) Preparation of Lactic Acid Bacteria Suspensions

*Tetragenococcus halophilus* strain NBRC 12172 were inoculated into MRS medium containing 10% salt at $1\times10^6$ cells/ml, while other strains were inoculated into ordinary MRS medium at $1\times10^6$ cells/ml. Following stationary culturing of *Tetragenococcus halophilus* strain NBRC 12172 for 72 hours and stationary culturing of other strains for 48 hours, heat killing was carried out by heating for 10 minutes at 95° C. Two fractions were collected from the samples, and after washing one of the fractions with 10 mM Tris-HCl (pH 8.0) and the other with 10 mM Tris-HCl (pH 8.0) containing 0.3 M NaCl, the bacteria cells were suspended in each of the liquids. The suspensions were adjusted to an $OD_{600nm}$ value of about 10.

(2) Bovine Pancreas-Derived RNase A Treatment

Bovine pancreas-derived RNase A (Sigma) was added to the above lactic acid bacteria suspensions to a concentration of 10 µg/ml followed by incubating for 2 hours at 37° C. In this enzyme treatment, both single-stranded RNA and double-stranded RNA are degraded in the absence of NaCl, while only single-stranded RNA is degraded in the presence of 0.3 M NaCl.

Following enzyme treatment, the bacteria cells were respectively washed twice with 10 mM Tris-HCl (pH 8.0) and 10 mM Tris-HCl (pH 8.0) containing 0.3 M NaCl followed by suspending in RPMI complete medium. The suspensions were adjusted to an $OD_{600nm}$ value of 0.125.

(3) Collection and Preparation of Peritoneal Exudate Macrophage Cells

Collection and preparation were carried out in the same manner as Example 1.

(4) Measurement of Interleukin 12 Production Promoting Activity

Measurement was carried out in the same manner as Example 1.

Figure 9:
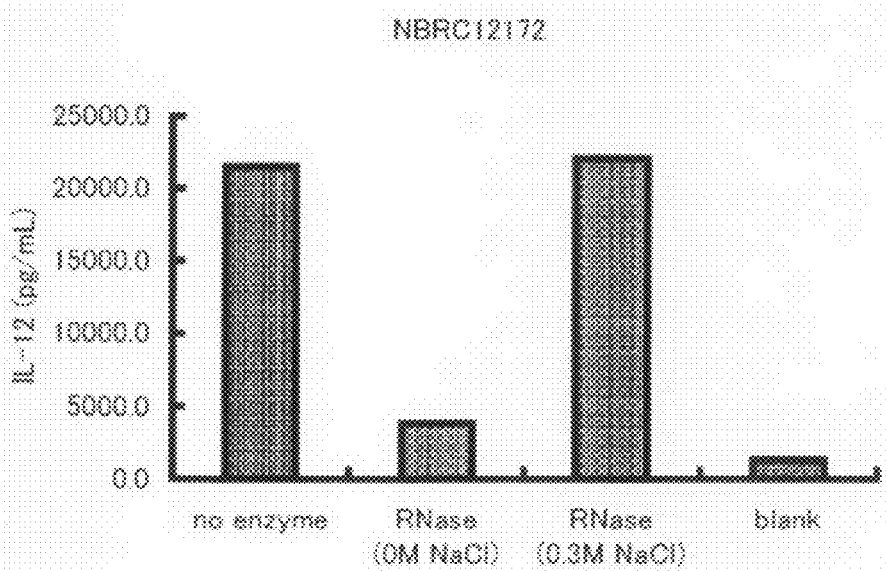
FIG. 9 is a graph showing the results of a test of promotion of interleukin 12 production in peritoneal exudate macrophage cells by *Tetragenococcus halophilus* strain NBRC 12172 cells and cells treated with bovine pancreas-derived RNase A (in the absence of NaCl and in the presence of 0.3 M NaCl)

The results for *Tetragenococcus halophilus* strain NBRC 12172 cells are shown in FIG. 9, the results for *Pediococcus pentosaceus* strain OS cells are shown in FIG. 10, the results for *Pediococcus pentosaceus* strain NRIC 1915 cells are shown in FIG. 11, the results for *Lactobacillus plantarum* strain NRIC 1930 cells are shown in FIG. 12, the results for *Lactobacillus delbrueckii* subspecies *bulgaricus* strain NRIC 1688 cells are shown in FIG. 13, the results for *Lactobacillus delbrueckii* subspecies *lactis* strain NRIC 1683 cells are shown in FIG. 14, the results for *Lactobacillus brevis* strain NRIC 1713 cells are shown in FIG. 15, the results for *Streptococcus thermophilus* strain NRIC 0256 cells are shown in FIG. 16, the results for *Leuconostoc pseudomesenteroides* strain ATCC 12291 cells are shown in FIG. 17, the results for bacteria cells of an isolate isolated from a commercially available drink, Yakult (Yakult Honsha) are shown in FIG. 18, and the results for bacteria cells of an isolate isolated from a commercially available plant-derived lactic acid bacteria drink, Labre (Kagome), are shown in FIG. 19.

Although interleukin 12 production promoting activity decreased considerably in all cases among samples that underwent enzyme treatment in the absence of NaCl, samples that underwent enzyme treatment in the presence of 0.3 M NaCl demonstrated smaller decreases in interleukin 12 production promoting activity. As a result, the double-stranded RNA fraction was indicated to have interleukin 12 production promoting activity.

EXAMPLE 6

Test of Promotion of Interleukin 12 Production by Various Lactic Acid Bacteria in Bone Marrow-Derived Dendritic Cells of TLR3-Knockout Mice The production of double-stranded RNA having immunoregulatory action was also confirmed in *Pediococcus pentosaceus* strain NRIC 0099 cells, *Pediococcus pentosaceus* strain NRIC 1915 cells, *Pediococcus pentosaceus* strain NRIC 0122 cells, *Lactobacillus pentosus* strain NRIC 0391 cells, *Lactobacillus pentosus* strain NRIC 0396 cells, *Lactobacillus casei* subspecies *casei* strain NRIC 0644 cells, *Lactobacillus plantarum* strain NRIC 1067 cells, *Lactobacillus pentosus* strain NRIC 1836 cells, *Lactobacillus plantarum* strain NRIC 1930 cells, *Lactobacillus paracasei* subspecies *paracasei* strain NRIC 1936 cells, *Leuconostoc lactis* strain NRIC 1582 cells, and *Leuconostoc mesenteroides* subspecies *mesenteroides* strain NRIC 1982 cells, by preparing bone marrow-derived dendritic cells from mice in which TLR3, recognizing double-stranded RNA, had been knocked out followed by measurement of interleukin 12 production promoting activity.

(1) Preparation of Lactic Acid Bacteria Suspensions

Each of the lactic acid bacteria were inoculated into MRS medium at $1\times10^7$ cells/ml. Following stationary culturing for 48 to 72 hours at 30° C., sterilization was carried out by boiling for 10 minutes at 95° C. Subsequently, the bacteria were collected by removing the media with a centrifugal concentrator. After washing the cells with physiological saline, the cells were suspended in base medium to prepare lactic acid bacteria suspensions.

(2) Preparation of Bone Marrow-Derived Dendritic Cells

Preparation was carried out in the same manner as Example 2.

(3) Measurement of Interleukin 12 Production Promoting Activity

Measurement was carried out in the same manner as Example 2. Since interleukin 12 production promoting activity decreased in bone marrow-derived dendritic cells from TLR3-knockout mice, TLR3 ligand in the form of double-stranded RNA was indicated to have immunoregulatory action, and double-stranded RNA was indicated to be produced in the bacteria cells shown in FIG. 20.

In this test, interferon β, which has been reported to be involved in interleukin 12 production, was also measured.

Interferon β production promoting activity from bone marrow-derived dendritic cells (culturing for 6 hours using the Interferon β Assay Kit manufactured by PBL) was as shown in FIG. 21.

EXAMPLE 7

Test of Promotion of Interleukin 12 Production by *Tetragenococcus halophilus* in the Presence of TRIF Pathway Inhibitor Interleukin 12 production promoting activity in the presence of TRIF pathway inhibitor was measured for *Tetragenococcus halophilus* strain Th221 cells and *Tetragenococcus halophilus* strain NBRC 12172 cells.
(1) Preparation of Lactic Acid Bacteria Suspensions
*Tetragenococcus halophilus* strain Th221 cells and *Tetragenococcus halophilus* strain NBRC 12172 cells were inoculated into MRS medium containing 10% salt at $1 \times 10^6$ cells/ml. Following stationary culturing for 72 hours, heat killing was carried out by heating for 10 minutes at 95° C. After washing the cells with physiological saline, the cells were suspended in RPMI complete medium. The suspensions were adjusted to $OD_{600nm}$ values of 0.25 and 0.125.
(2) Addition of TRIF Pathway Inhibitor
TBK1 (kinase) is known to interact with TRIF and phosphorylate transcription factor IRF-3. Resveratrol, which is known to inhibit this TBK1 activity, was added to the lactic acid bacteria suspensions as described below. Resveratrol (Sigma) was dissolved with DMSO to concentrations of 20 mM, 10 mM, 5 mM and 2.5 mm. In addition, DMSO alone was used as a control. These resveratrol solutions were added to the lactic acid bacteria suspensions to a concentration of 1% (v/v).
(3) Collection and Preparation of Peritoneal Exudate Macrophage Cells
Collection and preparation were carried out in the same manner as Example 1.
(4) Measurement of Interleukin 12 Production Promoting Activity
Measurement was carried out in the same manner as Example 1. The final resveratrol concentrations in the co-cultures of bacteria cells and macrophage cells were 100 μM, 50 μM, 25 μM, 12.5 μM and 0 μM.
The results for *Tetragenococcus halophilus* strain Th221 cells are shown in FIG. 22, while the results for *Tetragenococcus halophilus* strain NBRC 12172 cells are shown in FIG. 23. In both cases, interleukin 12 production promoting activity decreased dependent on the concentration of resveratrol. On the basis thereof, promotion of interleukin 12 production by *Tetragenococcus halophilus* strain Th221 cells and *Tetragenococcus halophilus* strain NBRC 12172 cells was indicated to be the result of activation of a TRIF-dependent signal transduction pathway.

EXAMPLE 8

Test of Promotion of Interleukin 12 Production by *Tetragenococcus halophilus* Strain Th221 Cells in Bone Marrow-Derived Dendritic Cells of TRIF-Knockout Mice Interleukin 12 production promoting activity was measured by preparing bone marrow-derived dendritic cells from mice in which TRIF, which is an adapter molecule of a signal transduction pathway involved in immunoregulatory action, had been knocked out.
(1) Preparation of Lactic Acid Bacteria Suspension
Culturing of *Tetragenococcus halophilus* strain Th221 was carried out in MRS medium containing 10% salt followed by preparation of a lactic acid bacteria suspension in the same manner as Example 1.
(2) Preparation of Bone Marrow-Derived Dendritic Cells
Preparation was carried out in the same manner as Example 2.
(3) Measurement of Interleukin 12 Production Promoting Activity
Measurement was carried out in the same manner as Example 1. The results are shown in FIG. 24.
Interleukin 12 production promoting activity decreased in bone marrow-derived dendritic cells from TRIF-knockout mice. On the basis thereof, activation of a TRIF-dependent signal transduction pathway was indicated to be involved in promotion of interleukin 12 production by *Tetragenococcus halophilus* strain Th221 cells.

EXAMPLE 9

Expression of TLR3 mRNA in a Test of Promotion of Interleukin 12 Production by *Tetragenococcus halophilus* Strain Th221 Cells Expression of TLR3 mRNA was measured by real-time PCR in a test of promotion of interleukin 12 production by *Tetragenococcus halophilus* strain Th221 cells.
(1) Preparation of Lactic Acid Bacteria Suspension
Culturing of lactic acid bacteria *Tetragenococcus halophilus* strain Th221 was carried out in MRS medium containing 10% salt followed by preparation of a lactic acid bacteria suspension in the same manner as Example 1.
(2) Collection and Preparation Peritoneal Exudate Macrophage Cells
Collection and preparation were carried out in the same manner as Example 1.
(3) Real-Time RT-PCR of TLR3 mRNA
Co-culturing of the macrophage cell suspension and lactic acid bacteria suspension was carried out in the same manner as Example 1. After co-culturing for 24 hours, the supernatant was removed followed by washing with PBS. 200 μl of TRIzol (Invitrogen) was then added thereto and the sample was recovered in an Eppendorf tube. After adding 40 μl of chloroform, stirring and centrifuging, the aqueous layer was recovered followed by the addition of an equal volume of chloroform thereto. After stirring and centrifuging, the aqueous layer was recovered followed by the addition of 1.7 equivalents of isopropanol and mixing. After centrifuging at 4° C. and 12,000 rpm, the precipitate was recovered and washed with 70% ethanol followed by dissolving with aqueous DEPC (Ambion) to obtain a template for use in real-time RT-PCR.
The following was used for the PCR forward primer for TLR3:

5'-GAGGGCTGGAGGATCTCTTTT-3'.            (SEQ ID NO. 1)

The following was used for the PCR reverse primer:

5'-CCGTTCTTTCTGAACTGGCCA-3'.            (SEQ ID NO. 2)

β-actin was used for the internal standard, and the following was used for the PCR forward primer:

5'-GCTACAGCTTCACCACCACAG-3'.            (SEQ ID NO. 3)

The following was used for the PCR reverse primer:

5'-GGTCTTTACGGATGTCAACGTC-3'.   (SEQ ID NO. 4)

Analysis was carried out by real-time RT-PCR in accordance with the protocol provided using the SYBR ExScript RT-PCR Kit (Perfect Real Time, Takara Shuzo).

The results are shown in FIG. 25.

Expression of TLR3 mRNA increased ten-fold as a result of co-culturing with *Tetragenococcus halophilus* strain Th221 cells. Namely, promotion of interleukin 12 production by *Tetragenococcus halophilus* strain Th221 cells was indicated to be the result of activation of TLR3.

EXAMPLE 10

Production of Double-Stranded RNA Derived From *Tetragenococcus halophilus* Strain Th221 Cells and Production of Bacteria Cells Containing Double-Stranded RNA

*Tetragenococcus halophilus* strain Th221 were inoculated into 400 ml of MRS medium (BD) containing 10% salt at $1 \times 10^6$ cells/ml. Following stationary culturing for 72 hours, sterilization was carried out by heating for 10 minutes at 95° C. Subsequently, the cells were collected by removing the medium by centrifugation. The cells were then suspended in 5 ml of STE buffer (100 mM NaCl, 10 mM Tris-HCl, 1 mM EDTA (pH 8.0)).

1 ml of 50 mg/ml lysozyme was then added thereto followed by incubating for 30 minutes at 37° C.

Subsequently, 0.1 ml of 50 mg/ml STE buffer, 0.3 ml of 10% SDS and 30 µl of 20 mg/ml Proteinase K were added followed by incubating for 1 hour at 37° C. 6 ml of a mixture of chloroform and isoamyl alcohol were then added thereto followed by mixing, centrifuging and recovery of the supernatant.

Subsequently, an equal volume of a mixture of chloroform and isoamyl alcohol was added followed by mixing, centrifuging and recovery of the supernatant. This procedure was carried out twice. After precipitating by adding 0.6 equivalents of isopropanol, the precipitate was dissolved in 10 ml of TE (10 mM Tris-HCl, 1 mM EDTA).

Ethanol is added to this crude nucleic acid extract to a final concentration of 15% and mixed well. CF11 cellulose powder (Wattman) is then added to a final concentration of 5% followed by gently shaking for 10 minutes in ice to adhere double-stranded RNA to the cellulose powder. The cellulose powder adhered with double-stranded RNA can be recovered as a precipitate by centrifugal separation (3,000×g, 4° C., 5 minutes). The recovered cellulose is re-suspended in a mixture of 15% ethanol and STE buffer (pH 8.0), and the resulting suspension is poured into a Econopak column (BioRad). 100 ml of a mixture of 15% ethanol and STE buffer (pH 8.0) are then passed through the column, and adhered components other than double-stranded RNA are washed out. Double-stranded RNA adhered to the cellulose column can be obtained by ethanol precipitation from a liquid sample obtained by passing 10 ml of STE buffer not containing ethanol through the column.

In order to remove residual DNA in the sample, treatment with DNase (Takara Shuzo) is first carried out. Continuing, in order to remove single-stranded RNA, treatment with bovine pancreas-derived RNase A (Sigma) is carried out in the presence of 0.3 M NaCl. Subsequently, purified double-stranded RNA can be obtained by extracting with phenol and chloroform and precipitating with ethanol. The resulting purified double-stranded RNA can be administered by incorporating in liposomes.

EXAMPLE 11

Measurement of Activation of Bone Marrow-Derived Dendritic Cells

When double-stranded RNA content increases dependent on salt concentration in cultures of lactic acid bacteria, interferon β is produced mediated by TLR3 of bone marrow-derived dendritic cells due to the addition of lactic acid bacteria, and this is thought to have an influence on the activation state of the bone marrow-derived dendritic cells.

Bone marrow-derived dendritic cells were stimulated with *Tetragenococcus halophilus* strain Th221 cells prepared at different salt concentrations followed by measurement of the activation state of the dendritic cells at that time.

Preparation of *Tetragenococcus halophilus* strain Th221 cells was carried out using the same method as Example 1. Bone marrow-derived dendritic cells were obtained in the same manner as Example 2 after collecting bone marrow cells from BALB/c mice.

Co-culturing of the bone marrow-derived dendritic cells and lactic acid bacteria was carried out in the same manner as Example 1. The bone marrow-derived dendritic cells were recovered after co-culturing for 24 hours followed by investigation of activation markers on the cell surface.

More specifically, activation markers consisting of CD40, CD80 and CD86 were detected with PE-labeled anti-CD40 antibody (BD Pharmingen), PE-labeled anti-CD80 antibody (BD Pharmingen) and PE-labeled anti-CD86 antibody (BD Pharmingen), respectively. The cells were measured with FACS Calibur (BD Pharmingen), and analyzed with Cell Quest software (BD Pharmingen).

The expressed amount of each activation marker increased dependent on the salt concentration in the culture of *Tetragenococcus halophilus* strain Th221. On the basis thereof, the amount of double-stranded RNA within the *Tetragenococcus halophilus* strain Th221 cells was thought to have increased salt concentration-dependently. The results are shown in FIG. 26.

EXAMPLE 12

Double-Stranded RNA Content in *Tetragenococcus halophilus* Strain Th221 Cells

Based on the results of Example 11, double-stranded RNA content in *Tetragenococcus halophilus* strain Th221 cells was thought to have increased dependent on the salt concentration during culturing. Therefore, a double-stranded RNA fraction was purified from bacteria cells cultured under conditions of varying salt concentrations followed by an investigation of the double-stranded RNA content thereof.

Culturing, heat killing and cell collection of *Tetragenococcus halophilus* strain Th221 cells were carried out in the same manner as Example 1. The cells were suspended in STE buffer and adjusted to an $OD_{600nm}$ value of 80. The remainder of the procedure was carried out in parallel by dividing each sample into three portions. Crude nucleic extracts were obtained using the same method as step (5) of Example 3, RNA fractions were obtained by carrying out TRIzol treatment (Invitrogen) on the crude nucleic acid extracts in accordance with the instructions provided, and double-stranded RNA fractions were obtained by subsequently degrading single-stranded nucleic acids by S1 nuclease treatment (Takara Shuzo, treated in accordance with the instructions provided). These double-stranded RNA fractions were electrophoresed in agarose gel to investigate the content thereof.

The results are shown in FIG. 27. The content of double-stranded RNA in *Tetragenococcus halophilus* strain Th221 cells was able to be confirmed to increase dependent on the salt concentration during culturing.

EXAMPLE 13

Purification of Double-Stranded RNA Derived From *Tetragenococcus halophilus* Strain Th221 Cells and Measurement of Immunoregulatory Activity Double-stranded RNA fractions derived from *Tetragenococcus halophilus* strain Th221 were purified, and the sequences of several of those fractions were determined followed by measurement of immunoregulatory activity.

Immunoregulatory activity was measured in the form of activity that promotes production of interleukin 12 from bone marrow-derived dendritic cells. Alternatively, since interferon β is known to be a cytokine involved in production of interleukin 12, activity that promotes production of interferon β from bone marrow-derived dendritic cells was also measured.

(1) Purification of Double-Stranded RNA Fractions Derived From *Tetragenococcus halophilus* Strain Th221

Purification was begun from 10 L of culture broth of *Tetragenococcus halophilus* strain Th221. Culturing, heat sterilization, cell collection, lysis, chloroform and isoamyl alcohol treatment, phenol, chloroform and isoamyl alcohol treatment, and isopropanol precipitation were carried out in the same manner as Example 10 to obtain a crude nucleic acid extract.

This crude nucleic acid extract was then subjected to TRIzol treatment (Invitrogen, treated in accordance with the instructions provided), DNase treatment (Takara Shuzo, treated in accordance with the instructions provided), RNase treatment in the presence of 0.3 M NaCl (Sigma, treated in the same manner as Example 3), repeated TRIzol treatment (Invitrogen, treated in accordance with the instructions provided), RNeasy Mini-RNase-Free DNase Set (Qiagen, treated in accordance with the instructions provided) and RNeasy Mini Kit (Qiagen, treated in accordance with the instructions provided) to obtain double-stranded RNA fractions.

(2) Measurement of Interleukin 12 Production Promoting Activity of Purified Double-Stranded RNA Fractions Interleukin 12 production promoting activity was measured for the double-stranded RNA fractions purified in step (1) above. Bone marrow-derived dendritic cells were prepared in the same manner as Example 2.

The purified double-stranded RNA fractions were added to the bone marrow-derived dendritic cells and co-cultured for 42 hours in a 5% $CO_2$ incubator at 37° C. Interleukin 12 production promoting activity was measured in the same manner as Example 1.

The results are shown in FIG. 28. Interleukin 12 production promoting activity increased dependent on the concentrations of the purified double-stranded RNA fractions.

At this time, interferon 13, which has been reported to be involved in interleukin 12 production, was also measured. Those results are shown in FIG. 29. Activity promoting production of interferon β from bone marrow-derived dendritic cells (culturing for 6 hours using an interferon β assay kit manufactured by PBL) increased dependent on the concentrations of the purified double-stranded RNA fractions.

(3) Cloning of cDNA

Synthesis of cDNA from the purified double-stranded RNA fractions was carried out in accordance with the method of Lambden et al. (J. Virol., 1992, 66, 1817-1822). The synthesized cDNA was cloned to a pCR4Blunt-TOPO vector and used to transform *Escherichia coli* HB101. About 60 clones were obtained and among these, the nucleotide sequences of two of the clones were determined to consist of the sequences indicated below.

```
DSR1 (46 mer):
                                          (SEQ ID NO. 5)
5'-AAATTTTCAAAAACCTGTTTTCGTTCTTCTAAAAATCCAATTGAA
A-3'

DSR2 (119 mer):
                                          (SEQ ID NO. 6)
5'-AAAAAATTACCTTTTTCTATTCGTGAGAAAATTTCTCAAGCCGAC

AAGTATCATAAAAAATTTGCTTTTGAACACTTTTTGAAGGTGTTTCTC

TATGGCATCGATCATGAGTGTGAAAG-3'
```

(4) Interferon β Production Promoting Activity of Double-Stranded RNA DSR1

Interferon β is a cytokine reported to be involved in the production of interleukin 12. Therefore, activity promoting the production of interferon β from bone marrow-derived dendritic cells was measured.

Synthesis of double-stranded RNA DSR1 was commissioned to Gene Design Inc.

Bone marrow-derived dendritic cells were prepared in the same manner as Example 2. Synthetic RNA was added to the bone marrow-derived dendritic cells followed by co-culturing for 6 hours in a 5% $CO_2$ incubator at 37° C. Interferon β production promoting activity was measured using an interferon β assay kit manufactured by PBL.

The results of investigating the concentration-dependent response of double-stranded RNA are shown in FIG. 30. Activity increased dependent on the concentration of the synthetic double-stranded RNA.

In addition, the results of investigating activity using bone marrow-derived dendritic cells from wild type and TLR3-knockout mice are shown in FIG. 31. Since interferon β production promoting activity decreased in bone marrow-derived dendritic cells from TLR3-knockout mice, the synthetic double-stranded RNA was indicated to produce interferon β mediated by TLR3.

(5) Interferon β Production Promoting Activity of Short Double-Stranded RNA Obtained by Dividing DSR1 into Three Sections Synthesis of double-stranded RNA DSR1 along with short double-stranded RNA fragments obtained by dividing DSR1 into three sections (S1, S2 and S3) was commissioned to Gene Design Inc. S1, S2 and S3 had the sequences indicated below.

```
S1 (18 mer): From 1st to 18th nucleotide of DSR1
                                          (SEQ ID NO. 7)
5'-AAATTTTCAAAAACCTGT-3'

S2 (15 mer): From 18th to 32nd nucleotide of DSR1
                                          (SEQ ID NO. 8)
5'-TTTTGCTTCTTCTAA-3'

S3 (15 mer): From 32nd to 46th nucleotide of DSR1
                                          (SEQ ID NO. 9)
5'-AAAATCCAATTGAAA-3'
```

Bone marrow-derived dendritic cells were prepared in the same manner as Example 2. Synthetic RNA was added to the bone marrow-derived dendritic cells followed by co-culturing for 6 hours in a 5% $CO_2$ incubator at 37° C. Interferon β production promoting activity was measured using an interferon β assay kit manufactured by PBL.

The results are shown in FIG. 32. Although differences were observed in the amount of interferon β depending on the sequence and length, interferon β was able to be confirmed to be produced from bone marrow-derived dendritic cells by double-stranded RNA.

(6) Interferon β Production Promoting Activity of Double-Stranded RNA DSR2

Double-stranded RNA DSR2 was synthesized as follows. First, two types of PCR amplification reaction products were produced in which a promoter region of T7 RNA polymerase was added to the 5' side or 3' side of DSR2 DNA.

A plasmid obtained by shotgun cloning of the genome of *Tetragenococcus halophilus* strain Th221 that contained the DSR2 domain was used for the template. The primers that were actually used as shown below.

T7DSR2F (50 mer):
(SEQ ID NO. 10)
5'-GATCACTAATACGACTCACTATAGGGGAAAAAATTACCTTTTTCTA

TTCGT-3'

DSR2C (24 mer):
(SEQ ID NO. 11)
5'-CTTTCACACTCATGATCGATGCCA-3'

DSR2F (24 mer):
(SEQ ID NO. 12)
5'-AAAAAATTACCTTTTTCTATTCGT-3'

T7DSR2C (50 mer):
(SEQ ID NO. 13)
5'-GATCACTAATACGACTCACTATAGGGCTTTCACACTCATGATCGAT

GCCA-3'

The PCR product was purified using the MERmaid Kit (MP Biomedical) in accordance with the instructions provided. In vitro transcription was then carried out by T7 RNA polymerase using this as a template (using the In Vitro Transcription T7 Kit manufactured by Takara Shuzo, and carried out in accordance with the instructions provided).

The synthesized transcription product was purified using the mirVana miRNA Isolation Kit, and an annealing procedure was carried out corresponding to the number of moles to form double-stranded RNA. This was used in subsequent testing after purifying by ethanol precipitation.

Bone marrow-derived dendritic cells were prepared in the same manner as Example 2. Synthetic RNA was added to the bone marrow-derived dendritic cells followed by co-culturing for 24 hours in a 5% $CO_2$ incubator at 37° C. Interferon β production promoting activity was measured using the interferon β assay kit manufactured by PBL.

The results are shown in FIG. 33. Interferon β was indicated to be produced from bone marrow-derived dendritic cells by synthetic double-stranded RNA DSR2.

EXAMPLE 14

Effect of Lactic Acid Bacteria RNA on Induction of Interferon γ-Producing Cells

What effect the presence or absence of RNase A treatment has on induction of interferon γ-producing cells during addition lactic acid bacteria was confirmed in a test involving co-culturing of bone marrow-derived dendritic cells and CD4+ T cells.

*Tetragenococcus halophilus* strain Th221 cells were cultured in MRS medium containing 10% salt. Preparation of bacteria cells subjected to RNase A treatment and those not subjected to treatment was carried out in the same manner as Example 1. Preparation of bone marrow-derived dendritic cells was carried out in the same manner as Example 2.

In addition, CD4+ T cells were prepared from the spleens of DO11.10 mice. Spleens were collected from DO11.10 mice and then shredded with a mesh to obtain spleen cells. Subsequently, the spleen cells were incubated for 30 minutes with anti-mouse CD4 beads (Miltenyi) to obtain CD4+ T cells using the Auto MACS system (Miltenyi).

$1 \times 10^5$ bone marrow-derived dendritic cells and $5 \times 10^5$ CD4+ T cells per well were cultured in a 96-well plate. Lactic acid bacteria subjected to RNase A treatment or lactic acid bacteria not subjected to RNase A treatment were simultaneously added at $5 \times 10^7$ cells/well.

The medium was replaced on day 3 after the start of culturing, and proportions of interferon γ-producing cells and interleukin 4-producing cells were investigated using the FACSAria flow cytometry system (BD) on day 7. Anti-mouse interferon γ antibody (BD Pharmingen) and anti-mouse interleukin 4 antibody (BD Pharmingen) were used for measurement.

The results are shown in FIG. 34. The proportion of interferon γ-producing cells increased due to stimulation by *Tetragenococcus halophilus* Th221. Induction of interferon γ-producing cells was inhibited by treatment of the bacteria cells with RNase A. On the basis thereof, RNA of lactic acid bacteria was confirmed to be involved in the induction of interferon γ-producing cells.

The invention claimed is:

1. A double-stranded RNA derived from lactic acid bacteria, wherein the lactic acid bacteria are one strain or two or more strains from a genus selected from the group consisting of genus *Tetragenococcus*, genus *Pediococcus*, genus *Streptococcus* and genus *Leuconostoc*, which has an immunoregulatory action that is an activation of a TRIF-dependent signal transduction pathway or MyD88-dependent signal transduction pathway.

2. The double-stranded RNA derived from lactic acid bacteria according to claim 1, wherein activation of the TRIP-dependent signal transduction pathway or the MyD88-dependent signal transduction pathway is activation of Toll-like receptor 3 (TLR3).

3. An immunoregulator having for an active ingredient thereof double-stranded RNA derived from lactic acid bacteria, which has an immunoregulatory action that is an activation of a TRIF-dependent signal transduction pathway or MyD88-dependent signal transduction pathway.

4. The immunoregulator according to claim 3, wherein the lactic acid bacteria are one strain or two or more strains from a genus selected from the group consisting of genus *Tetragenococcus*, genus *Pediococcus*, genus *Streptococcus* and genus *Leuconostoc*.

5. A process for producing the double-stranded RNA derived from lactic acid bacteria according to claim 1.

6. The process for producing the double-stranded RNA derived from lactic acid bacteria according to claim 5, wherein the lactic acid bacteria are one strain or two or more strains from a genus selected from the group consisting of genus *Tetragenococcus*, genus *Pediococcus*, genus *Streptococcus* and genus *Leuconostoc*.

* * * * *

SEQUENCE LISTING

<160> NUMBER OF SEQ ID NOS: 13

<210> SEQ ID NO 1
<211> LENGTH: 21
<212> TYPE: DNA
<213> ORGANISM: Mus musculus

<400> SEQUENCE: 1
gagggctgga ggatctcttt t                    21

<210> SEQ ID NO 2

```
<211> LENGTH: 21
<212> TYPE: DNA
<213> ORGANISM: Mus musculus

<400> SEQUENCE: 2
ccgttctttc tgaactggcc a                                         21

<210> SEQ ID NO 3
<211> LENGTH: 21
<212> TYPE: DNA
<213> ORGANISM: Mus musculus

<400> SEQUENCE: 3
gctacagctt caccaccaca g                                         21

<210> SEQ ID NO 4
<211> LENGTH: 22
<212> TYPE: DNA
<213> ORGANISM: Mus musculus

<400> SEQUENCE: 4
ggtctttacg gatgtcaacg tc                                        22

<210> SEQ ID NO 5
<211> LENGTH: 46
<212> TYPE: DNA
<213> ORGANISM: Tetragenococcus halophilus

<400> SEQUENCE: 5
aaattttcaa aaacctgttt tgcttcttct aaaaatccaa ttgaaa              46

<210> SEQ ID NO 6
<211> LENGTH: 119
<212> TYPE: DNA
<213> ORGANISM: Tetragenococcus halophilus

<400> SEQUENCE: 6
aaaaaattac cttttctat tcgtgagaaa atttctcaag ccgacaagta tcataaaaaa  60
tttgcttttg aacacttttt gaaggtgttt ctctatggca tcgatcatga gtgtgaaag  119

<210> SEQ ID NO 7
<211> LENGTH: 18
<212> TYPE: DNA
<213> ORGANISM: Tetragenococcus halophilus

<400> SEQUENCE: 7
aaattttcaa aaacctgt                                             18

<210> SEQ ID NO 8
<211> LENGTH: 15
<212> TYPE: DNA
<213> ORGANISM: Tetragenococcus halophilus

<400> SEQUENCE: 8
ttttgcttct tctaa                                                15

<210> SEQ ID NO 9
<211> LENGTH: 15
<212> TYPE: DNA
<213> ORGANISM: Tetragenococcus halophilus

<400> SEQUENCE: 9
aaaatccaat tgaaa                                                15
```

```
<210> SEQ ID NO 10
<211> LENGTH: 50
<212> TYPE: DNA
<213> ORGANISM: Tetragenococcus halophilus

<400> SEQUENCE: 10
gatcactaat acgactcact atagggaaaa aattaccttt ttctattcgt          50

<210> SEQ ID NO 11
<211> LENGTH: 24
<212> TYPE: DNA
<213> ORGANISM: Tetragenococcus halophilus

<400> SEQUENCE: 11
ctttcacact catgatcgat gcca                                      24

<210> SEQ ID NO 12
<211> LENGTH: 24
<212> TYPE: DNA
<213> ORGANISM: Tetragenococcus halophilus

<400> SEQUENCE: 12
aaaaaattac ctttttctat tcgt                                      24

<210> SEQ ID NO 13
<211> LENGTH: 50
<212> TYPE: DNA
<213> ORGANISM: Tetragenococcus halophilus

<400> SEQUENCE: 13
gatcactaat acgactcact atagggcttt cacactcatg atcgatgcca          50
```